(12) United States Patent
Pickering-Brown et al.

(10) Patent No.: US 9,896,729 B2
(45) Date of Patent: Feb. 20, 2018

(54) METHOD FOR DIAGNOSING A NEURODEGENERATIVE DISEASE

(75) Inventors: Stuart Pickering-Brown, Manchester (GB); Bryan Traynor, Bethesda, MD (US); Andrew B. Singleton, Poolesville, MD (US); Huw Morris, Cardiff (GB); Peter Heutink, Tübingen (DE); John Hardy, Chelmsford (GB); Pentti Tienari, Helsinki (FI)

(73) Assignees: The University of Manchester, Manchester (GB); National Institute of Aging, Bethesda, MD (US); Hospital District of Helsinki and UUSIMAA, Helsinki (FI); VU University Medical Centre Armsterdam, Amsterdam (NL); UCL Business PLC, London (GB); University College Cardiff Consultants Limited, Cardiff (GB)

( * ) Notice: Subject to any disclaimer, the term of this patent is extended or adjusted under 35 U.S.C. 154(b) by 0 days.

(21) Appl. No.: 14/241,646

(22) PCT Filed: Aug. 31, 2012

(86) PCT No.: PCT/GB2012/052140
§ 371 (c)(1),
(2), (4) Date: May 19, 2015

(87) PCT Pub. No.: WO2013/030588
PCT Pub. Date: Mar. 7, 2013

(65) Prior Publication Data
US 2015/0252421 A1    Sep. 10, 2015

Related U.S. Application Data

(60) Provisional application No. 61/529,531, filed on Aug. 31, 2011.

(51) Int. Cl.
C07H 21/04 (2006.01)
C12Q 1/68 (2006.01)
(Continued)

(52) U.S. Cl.
CPC ........ *C12Q 1/6883* (2013.01); *A61K 38/1709* (2013.01); *G01N 33/502* (2013.01);
(Continued)

(58) Field of Classification Search
None
See application file for complete search history.

(56) References Cited

PUBLICATIONS

DeJesus-Hernandez, M., Mackenzie, I. R., Boeve, B. F., Boxer, A. L., Baker, M., Rutherford, N. J., Nicholson, A. M., Finch, N. A., Flynn, H., Adamson, J., Kouri, N., Wojtas, A., and 16 others. Expanded GGGGCC hexanucleotide repeat in noncoding region of C9ORF72 causes chromosome 9p-linked FTD and ALS. Neuron 72: 245-256, 2011.*

(Continued)

*Primary Examiner* — Jeanine A Goldberg
(74) *Attorney, Agent, or Firm* — Bryan D. Zerhusen; Locke Lord LLP

(57) ABSTRACT

The present invention relates to methods of assessing whether a subject has or is likely to develop a neurodegenerative disease comprising determining whether the subject has a mutation in the C9orf72 gene wherein said mutation prevents or disrupts C9orf72 expression relative to expression in a reference from subjects without the mutation.

20 Claims, 13 Drawing Sheets

Figure 1A:
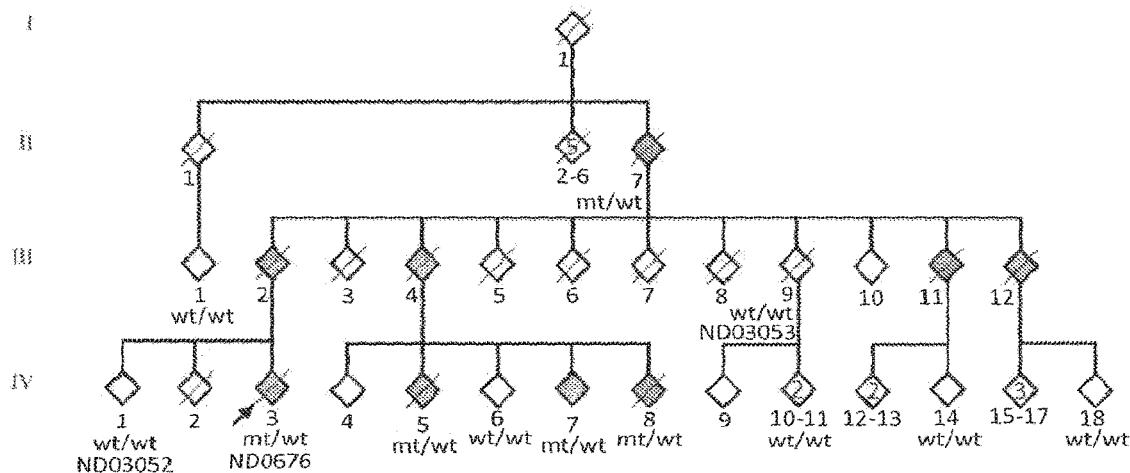

(51) Int. Cl.
A61K 38/17 (2006.01)
G01N 33/50 (2006.01)
G01N 33/68 (2006.01)

(52) U.S. Cl.
CPC ..... *G01N 33/5088* (2013.01); *G01N 33/6896* (2013.01); *C12Q 2600/106* (2013.01); *C12Q 2600/136* (2013.01); *C12Q 2600/156* (2013.01); *C12Q 2600/158* (2013.01); *C12Q 2600/16* (2013.01); *G01N 2333/47* (2013.01); *G01N 2800/2814* (2013.01); *G01N 2800/2835* (2013.01)

(56) References Cited

PUBLICATIONS

Renton, A. E., Majounie, E., Waite, A., Simon-Sanchez, J., Rollinson, S., Gibbs, J. R., Schymick, J. C., Laaksovirta, H., van Swieten, J. C., Myllykangas, L., Kalimo, H., Paetau, A., and 65 others. A hexanucleotide repeat expansion in C9ORF72 is the cause of chromosome 9p21-linked ALS-FTD. Neuron 72: 257-268, 2011.*
Laaksovirta et al. (Lancet Neurol, vol. 9, No. 10, pp. 978-985, Oct. 2010).*
Shatunov et al. (The Lancet, vol. 9, pp. 986-994, Aug. 31, 2010).*
Nastiuk et al (Prostates, vol. 40, No. 3, pp. 1'72-177, 1999).*
Ioannidis (Nature Genetics, vol. 29, pp. 306-309, Nov. 2001).*
Hirschhorn et al. (Genetics in Medicine. vol. 4, No. 2, pp. 45-61, Mar. 2002).*
Donnelly et al. (Neuron, vol. 80, No. 2, pp. 415-428, Oct. 2013).*
Johns Hopkins Medicine News and Publications. "Individualized Therapy for the Brain targets specific gene mutations causing dementia and ALS" Oct. 16, 2013.*
International Search Report and Written Opinion of the International Searching Authority, for PCT/GB2012/052140, dated Feb. 5, 2013.
International Preliminary Report on Patentability, for PCT/GB2012/052140, dated Mar. 4, 2014.
"Homo sapiens gene C9orf72, encoding chromosome 9 open reading frame 72.", Aug. 28, 2010 (Aug. 28, 2010), XP055050957, Retrieved from the Internet: URL:http://www.ncbi.nlm.nih.gov/IEB/Research/Acembly/ay.cgi?db=human&l=C9orf 72 [retrieved on Jan. 24, 2013] Note: This is a direct link to the https://worldwide.espacenet.com/ website for review.
"Homo sapiens gene C9orf72, encoding chromosome 9 open reading frame 72.", Aug. 28, 2010 (Aug. 28, 2010), XP055050960, Retrieved from the Internet: URL:http://www.ncbi.nlm.nih.gov/IEB/Research/Acembly/ay.cgi?db=human&l=C9orf 72 [retrieved on Jan. 24, 2013] Note: This is a direct link to the https://worldwide.espacenet.com/ website for review.
Aleksey Shatunov et al:"Chromosome 9p21 in sporadic amyotrophic lateral sclerosis in the UK and seven other countries: a genome-wide association study", Lancet Neurol, vol. 9, Oct. 13, 2010 (Oct. 12, 2010), pp. 986-994, XP055050921, DOI: 10.1016/S1474.
Elisa Majounie et al:"Frequency of the C9orf72 hexanucleotide repeat expansion in patients with amyotrophic lateral sclerosis and frontotemporal dementia: a cross-sectional study", Lancet Neurol., vol. 11, Mar. 9, 2012 (Mar. 9, 2012), pp. 323-330, XP055050886, DOI: 10.1016/S1474-.
Susan Byrne et al: "Cognitive and clinical characteristics of patients with amyotrophic lateral sclerosis carrying a C9orf72 repeat expansion: a population-based cohort study", The Lancet Neurology, vol. 1, No. 3, Mar. 1, 2012 (Mar. 1, 2012), pp. 232-240, XP055050900, ISSN: 1474-4422, DOI: 10.1016/S1474-4422(12)70014-5.
Andrea Calvo et al: "Amyotrophic lateral sclerosis/frontotemporal dementia with predominant anifestations of obsessive-compulsive disorder associated to GGGGCC expansion of the c9orf72 gene", Journal of Neurology, Aug. 1, 2012 (Aug. 1, 2012), XP055044209, ISSN: 0340-5354, DOI: 10.1007/s00415-012-6640-1.
Gianluca Floris et al: "Frontotemporal dementia with psychosis, parkinsonism, visuo-spatial dysfunction, upper motor neuron involvement associated to expansion of C9ORF72: a peculiar phenotype?", Journal of Neurology, Steinkopff-Verlag, DA, vol. 259, No. 8, Feb. 10, 2012 (Feb. 10, 2012), pp. 1749-1751, XP035093432, ISSN: 1432-1459, DOI:10.1007/S00415-012-6444-3.
Laura E Downey et al: "Impaired self-other differentiation in frontotemporal dementia due to the C9ORF72 expansion", Alzheimers Res Ther, Biomed Central Ltd, London, UK, vol. 4, No. 5, Aug. 3, 2012 (Aug. 13, 2012) , p. 42, XP021130316, ISSN: 1758-9193, DOI: 10.1186/ALZRT145.

* cited by examiner

GWENT#1

DUTCH#1

ITALS#2

Family 365

A

Mouse motor Neuron cell line (NSC-34)

Nuclear Staining pattern in NSC-34

B  Human primary fibroblasts

Nuclear staining pattern in control fibroblasts

C

D

SEQUENCE LISTING

<160> NUMBER OF SEQ ID NOS: 16

<210> SEQ ID NO 1
<211> LENGTH: 3794

<212> TYPE: DNA
<213> ORGANISM: Homo sapiens

<400> SEQUENCE: 1

```
agcttgggct gaaattgtgc aggcgtctcc acaccccat ctcatcccgc atgatctcct        60
cgccggcagg gaccgtctcg ggttcctagc gaaccccgac ttggtccgca gaagccgcgc       120
gccgcccacc ctccggcctt ccccaggcg aggcctctca gtacccgagg ctcccttttc        180
tcgagcccgc agcggcagcg ctcccagcgg gtccccggga aggagacagc tcgggtactg       240
agggcgggaa agcaaggaag aggccagatc cccatccctt gtccctgcgc cgccgccgcc       300
gccgccgccg ccgggaagcc cggggcccgg atgcaggcaa ttccaccagt cgctagaggc       360
gaaagcccga cacccagctt cggtcagaga aatgagaggg aaagtaaaaa tgcgtcgagc       420
tctgaggaga gccccgcttc taccccgcgc ctcttcccgg cagccgaacc ccaaacagcc       480
acccgccagg atgccgcctc ctcactcacc cactcgccac cgcctgcgcc tccgccgccg       540
cgggcgcagg caccgcaacc gcagccccgc cccgggcccg ccccggggcc cgccccgacc       600
acgcccggc ccggccccg ccctagcg cgcgactcct gagttccaga gcttgctaca          660
ggctgcggtt gtttccctcc ttgttttctt ctggttaatc tttatcaggt cttttcttgt       720
tcaccctcag cgagtactgt gagagcaagt agtggggaga gagggtggga aaaacaaaaaa      780
cacacacctc ctaaacccac acctgctctt gctagaccc gccccaaaaa gagaagcaac        840
cgggcagcag ggacggctga cacaccaagc gtcatctttt acgtgggcgg aacttgtcgc       900
tgtttgacgc acctctcttt cctagcggga caccgtaggt tacgtctgtc tgttttctat       960
gtgcgatgac gttttctcac gaggctagcg aaatggggcg gggcaacttg tcctgttctt      1020
ttatcttaag acccgctctg gaggagcgtt ggcgcaatag cgtgtgcgaa ccttaataag      1080
ggaggctgct ggatctggag aaagtgaaga cgatttcgtg gttttgaatg gttttgtttg      1140
tgcttggtag gcagtgggcg ctcaacacat aattggtgga tgaaattttg ttttaccgt       1200
aagacactgt taagtgcatt caaaactcca ctgcaaaccc tggtagggga cagctccggc      1260
actgcgggcg ggaatcccac ggtccctgc aaagtcatcg caattttgcc tttacatgta       1320
agaattctct caagcatgat tttcacactg gggaatgtca ttttttgctag ttgcaatatg     1380
tggatgagtt gttttttttt aacttttgaa aaacgtacca ttctgttttga tgtgtaaaaa    1440
acacaaagat ttttgaaacc ttgcgtcttt tggtctgcag gtgtatagat tccacttact      1500
acagatgagt agcatttaca ccactcagat gtgtaaaaaa acaaaggttt tttaaactgt     1560
gtgcctttttg atctgcaagt gtgagatggc acttactaca gtgagtagca tttaatcttt     1620
ttcatcacta aaaatcacac agaacgtttt aatcattcac cgaggaagaa agggaggaat     1680
aaatacacaa aatggctctc aacgtctaca ccttctgcag aaacagaccc ttttcctact      1740
gttctatgct ttgtgaaagt tgatcataca aattgggtca ttcttttat acccaactaa       1800
aatagtgggg gtaggggta gaaaagcact taggacaaat gacactgctc ccacagtgta       1860
attctctcca agtccagctg ctgcaactgc ccgttgtgac ctgagaccag ttttatctaa      1920
tagttgctaa aatgacctgc tgcagctcta atttatcta ccaccatcac tcaccagttg       1980
aaactcacca gctcctcaga tccttaatag tgccaatgaa ttttctcaaa gagcactatg      2040
taacatttct cttttttaac aaaacctccc ccttttcttt gttgtgtgga tataccgaag      2100
accatctgat ctcatgtat gcccctaattg caattctttc ttcccaaata aatcacttaa      2160
tttagagatt catctctgta ttttattttt gactgacagc ttataacaag tagctagcat      2220
```

```
ttaccaagtt tctacactga gttgtacttc acttatacgt ggaattaaaa aacaactgaa    2280
tttatagaaa cagagtagac ccttggttgg ggggcttggg gggaaagaaa attgtagggt    2340
agggtacaaa gttgcagtta cgtctaatac atctagagat ttaatgtaca acatgaggac    2400
tagcgttaat aattgtgtta gtccattctt acactgctat aaagaaataa ctgaaactgg    2460
gtaatttata agaaaagttt taatggctca cagttctgca ggctgtacaa gaagcatggc    2520
tggatcagct tctgggcagg ccatagggaa cttaaaatca tgatggaagg catagggaga    2580
ccccagactt cacatggcag gaactggggg aagagagaaa tgggaggtgc tacatacgtt    2640
taaacaacta gatcttgtca gaactcacta tatagtacca agagggggact gtacaaaacc    2700 attagaagcc accccataat ccactcacct cccaccaggc ccaacctcca acactgggga    2760
ttacagttga acatgagatt tgggtgggga cagagatcca aaccatgtta ttccaactct    2820
ggcccctccc aaatctaatg tccttctcat attgcaaaat actgtcgtgc cttaccaaca    2880 gttcccaaa gtcttaactc gatccagcat tcattcaaaa gtccaaagtc ccaagtctca    2940
cctgagacga agctagtccc ttctacctat gaacctgtaa atcaaaaac aaggtaattg    3000 cttcaaagat acaatggggg tataggcatt gggcagatac tgccattccg aaagggagaa    3060
atctgccaaa gaaagaggc tataggcccc cattgcaagt ctgaaagcca gccgggcagt    3120
cattaaatgt taaagctctg aaataatctc ctttgactca cacccaggga acactgatgc    3180
aatgagtggg ctcccaaaac cttgggcaga accaccctg tggttttcca gggttcatct    3240
cccacagctg ctctcatggg ctagcattga gtgcttgcag cttttccagg ctgcagggtg    3300
caagttgttg gtggatctac cattctgggg tctggaggac ggtggctgtc ttgtcatagc    3360
tctgctaggc agtgccccag gggactctct gtggggctg caaccccaca tttcttctcc    3420
ttgcttccct agtagatgtt ctccatgagg attccacccc agtaacaggc ttctgtctgg    3480
acatccaggc tttttcatac atcctctaaa atctaggcag agcttcttaa gcctcaactc    3540
ttgcattatg tgcgcccgcc ggcttcacag cttatggaag ccaccaaggc ttatgcctgg    3600
caccctgtga agcagcagcc tgaactgtat tcttactggt gaaagttatc tgagttacca    3660
gctgcaaatc catgtgggtc tgcagcaacc tcaattcttg cctcctcaga agaaagaatt    3720
tgaccaagag gcataaggca gaaaaagaga ctgcgacaag tttcagagca ggagtaaaag    3780
tttattaaaa agct                                                      3794
```

<210> SEQ ID NO 2
<211> LENGTH: 481
<212> TYPE: PRT
<213> ORGANISM: Homo sapiens

<400> SEQUENCE: 2

Met Ser Thr Leu Cys Pro Pro Ser Pro Ala Val Ala Lys Thr Glu
1               5                   10                  15

Ile Ala Leu Ser Gly Lys Ser Pro Leu Leu Ala Ala Thr Phe Ala Tyr
            20                  25                  30

Trp Asp Asn Ile Leu Gly Pro Arg Val Arg His Ile Trp Ala Pro Lys
        35                  40                  45

Thr Glu Gln Val Leu Leu Ser Asp Gly Glu Ile Thr Phe Leu Ala Asn
    50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Ile Val Ser
                85                  90                  95

-continued

Leu Ile Phe Asp Gly Asn Trp Asn Gly Asp Arg Ser Thr Tyr Gly Leu
            100                 105                 110

Ser Ile Ile Leu Pro Gln Thr Glu Leu Ser Phe Tyr Leu Pro Leu His
        115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Ile Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ser Ser Met Lys Ser
            180                 185                 190

His Ser Val Pro Glu Glu Ile Asp Ile Ala Asp Thr Val Leu Asn Asp
        195                 200                 205

Asp Asp Ile Gly Asp Ser Cys His Glu Gly Phe Leu Leu Asn Ala Ile
    210                 215                 220

Ser Ser His Leu Gln Thr Cys Gly Cys Ser Val Val Gly Ser Ser
225                 230                 235                 240

Ala Glu Lys Val Asn Lys Ile Val Arg Thr Leu Cys Leu Phe Leu Thr
                245                 250                 255

Pro Ala Glu Arg Lys Cys Ser Arg Leu Cys Glu Ala Glu Ser Ser Phe
            260                 265                 270

Lys Tyr Glu Ser Gly Leu Phe Val Gln Gly Leu Leu Lys Asp Ser Thr
        275                 280                 285

Gly Ser Phe Val Leu Pro Phe Arg Gln Val Met Tyr Ala Pro Tyr Pro
    290                 295                 300

Thr Thr His Ile Asp Val Asp Val Asn Thr Val Lys Gln Met Pro Pro
305                 310                 315                 320

Cys His Glu His Ile Tyr Asn Gln Arg Tyr Met Arg Ser Glu Leu
                325                 330                 335

Thr Ala Phe Trp Arg Ala Thr Ser Glu Glu Asp Met Ala Gln Asp Thr
            340                 345                 350

Ile Ile Tyr Thr Asp Glu Ser Phe Thr Pro Asp Leu Asn Ile Phe Gln
        355                 360                 365

Asp Val Leu His Arg Asp Thr Leu Val Lys Ala Phe Leu Asp Gln Val
    370                 375                 380

Phe Gln Leu Lys Pro Gly Leu Ser Leu Arg Ser Thr Phe Leu Ala Gln
385                 390                 395                 400

Phe Leu Leu Val Leu His Arg Lys Ala Leu Thr Leu Ile Lys Tyr Ile
                405                 410                 415

Glu Asp Asp Thr Gln Lys Gly Lys Lys Pro Phe Lys Ser Leu Arg Asn
            420                 425                 430

Leu Lys Ile Asp Leu Asp Leu Thr Ala Glu Gly Asp Leu Asn Ile Ile
        435                 440                 445

Met Ala Leu Ala Glu Lys Ile Lys Pro Gly Leu His Ser Phe Ile Phe
    450                 455                 460

Gly Arg Pro Phe Tyr Thr Ser Val Gln Glu Arg Asp Val Leu Met Thr
465                 470                 475                 480

Phe

<210> SEQ ID NO 3
<211> LENGTH: 222
<212> TYPE: PRT

<213> ORGANISM: Homo sapiens

<400> SEQUENCE: 3

```
Met Ser Thr Leu Cys Pro Pro Ser Pro Ala Val Ala Lys Thr Glu
1               5                   10                  15

Ile Ala Leu Ser Gly Lys Ser Pro Leu Leu Ala Ala Thr Phe Ala Tyr
                20                  25                  30

Trp Asp Asn Ile Leu Gly Pro Arg Val Arg His Ile Trp Ala Pro Lys
            35                  40                  45

Thr Glu Gln Val Leu Leu Ser Asp Gly Glu Ile Thr Phe Leu Ala Asn
        50                  55                  60

His Thr Leu Asn Gly Glu Ile Leu Arg Asn Ala Glu Ser Gly Ala Ile
65                  70                  75                  80

Asp Val Lys Phe Phe Val Leu Ser Glu Lys Gly Val Ile Val Ser
                85                  90                  95

Leu Ile Phe Asp Gly Asn Trp Asn Gly Asp Arg Ser Thr Tyr Gly Leu
                100                 105                 110

Ser Ile Ile Leu Pro Gln Thr Glu Leu Ser Phe Tyr Leu Pro Leu His
            115                 120                 125

Arg Val Cys Val Asp Arg Leu Thr His Ile Ile Arg Lys Gly Arg Ile
    130                 135                 140

Trp Met His Lys Glu Arg Gln Glu Asn Val Gln Lys Ile Ile Leu Glu
145                 150                 155                 160

Gly Thr Glu Arg Met Glu Asp Gln Gly Gln Ser Ile Ile Pro Met Leu
                165                 170                 175

Thr Gly Glu Val Ile Pro Val Met Glu Leu Leu Ser Ser Met Lys Ser
            180                 185                 190

His Ser Val Pro Glu Glu Ile Asp Ile Ala Asp Thr Val Leu Asn Asp
        195                 200                 205

Asp Asp Ile Gly Asp Ser Cys His Glu Gly Phe Leu Leu Asn
    210                 215                 220
```

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
agtcgctaga ggcgaaagc           19

<210> SEQ ID NO 5
<211> LENGTH: 43
<212> TYPE: DNA
<213> ORGANISM: Artificial Sequence
<220> FEATURE:
<223> OTHER INFORMATION: Primer

<400> SEQUENCE: 5
tacgcatccc agtttgagac gggggccggg gccggggccg ggg           43

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6

-continued tacgcatccc agtttgagac g                                    21

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
ggccccggcc ccggccccgg cc                                   22

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
gaaatcacac agtgttcctg aagaa                                25

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
agctgatggc attgagaaga aag                                  23

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
cctgttcgac agtcagccg                                       19

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cgaccaaatc cgttgactcc                                      20

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
atctgcttca tccagctttt atga                                 24

<210> SEQ ID NO 13
<211> LENGTH: 12
<212> TYPE: DNA

```
<213> ORGANISM: Artificial Sequence
<220> FEATURE:
<223> OTHER INFORMATION: Synthetic

<400> SEQUENCE: 13
ggccccggcc cc                                                          12

<210> SEQ ID NO 14
<211> LENGTH: 12
<212> TYPE: DNA
<213> ORGANISM: Artificial Sequence
<220> FEATURE:
<223> OTHER INFORMATION: Synthetic

<400> SEQUENCE: 14
ggggccgggg cc                                                          12

<210> SEQ ID NO 15
<211> LENGTH: 18
<212> TYPE: DNA
<213> ORGANISM: Artificial Sequence
<220> FEATURE:
<223> OTHER INFORMATION: Synthetic

<400> SEQUENCE: 15
ggccccggcc ccggcccc                                                    18

<210> SEQ ID NO 16
<211> LENGTH: 18
<212> TYPE: DNA
<213> ORGANISM: Artificial Sequence
<220> FEATURE:
<223> OTHER INFORMATION: Synthetic

<400> SEQUENCE: 16
ggggccgggg ccggggcc                                                    18
```

METHOD FOR DIAGNOSING A NEURODEGENERATIVE DISEASE

RELATED APPLICATIONS

This Application is a 35 U.S.C. §371 U.S. national entry of International Application PCT/GB2012/052140 (WO 2013/030588) having an International filing date of Aug. 31, 2012, which claims the benefit of U.S. Provisional Application Ser. No. 61/529,531, filed Aug. 31, 2011 the entire contents of which are hereby incorporated herein by reference.

The present invention relates to prognostic and diagnostic tests for neurodegenerative disease, treatment regimens for neurodegenerative disease, animal models for neurodegenerative disease and screening methods for identifying drugs useful for treating such diseases.

Neurodegenerative diseases are a major clinical problem that may manifest in a number of forms. For Example frontotemporal lobar degeneration, Alzheimer's disease, Motor Neuron Disease, Lewy body diseases, Parkinson Disease and the like.

Many neurodegenerative diseases are often accompanied by dementia. Dementia is the progressive decline in cognitive function due to damage or disease in the brain beyond what might be expected from normal aging. Particularly affected areas may be memory, attention, language, and problem solving. Especially in the later stages of the condition, affected persons may be disoriented in time (not knowing what day of the week, day of the month, month, or even what year it is), in place (not knowing where they are), and in person (not knowing who they are). The prevalence of dementia is rising as the global life expectancy is rising. Particularly in Western countries, there is increasing concern about the economic impact that dementia will have in future, older populaces. Dementia is a non-specific term encompassing many disease processes. At present there is no cure for any type of dementia.

Frontotemporal lobar degeneration (FTLD) is a type of neurodegenerative disease involving degeneration of gray matter in the frontal lobe and anterior portion of the temporal lobe of the cerebrum, with sparing of the parietal and occipital lobes. FTLD is the second most common form of dementia after Alzheimer's disease and is therefore a major cause of neurological problems in the elderly. The syndrome of FTLD encompasses the clinical subgroups of frontotemporal dementia (FTD), FTD with motor neuron disease (MND), semantic dementia and primary progressive aphasia, and is characterized by changes in behaviour, personality and language with relative preservation of memory and perception.

Pathologically, there are two main histological profiles associated with FTLD. One of these is tauopathy, the accumulation of hyperphosphorylated tau in neurons and occasionally in glia. However, the most common neuropathology associated with FTLD, accounting for well over half of all cases, is that known as FTLD-U, in which there are neuronal cytoplasmic inclusions and neurites that are immunoreactive for ubiquitin (ub-ir) but not for tau. FTLD pathology of this type was first described in patients with motor neuron disease (MND) and dementia but has subsequently been recognized as a common neuropathological feature of FTLD in patients without motor symptoms. This ub-ir pathology is characteristically found in granule cells of dentate fascia of the hippocampus and in neurons of layer 2 of the frontal and temporal neocortex.

MND is a clinically important neurodegenerative disease which can arise in subjects independent of FTD. MND is also known as amyotrophic lateral sclerosis (ALS). MND/ALS is a fatal neurodegenerative disease affecting motor neurons and is characterised by rapidly progressive weakness and ultimately death from respiratory failure (typically within three years of symptom onset).

It has been a significant aim of the research community to understand the genetics of neurodegenerative disorders and particularly MND/ALS and FTLD.

The genetics of neurodegenerative disorders is complex with 7 disease loci reported to date, these being on chromosomes 3, 9p (2 loci), 9q, 17q21 (2 loci) and 17q24. Only a few of the genes within these loci are known.

It has been reported that a mutation in the splice acceptor site of exon 6 of CHMP2B on chromosome 3 causes FTLD in a large Danish family with DLDH-type of histology. However, it has been shown that this is a rare genetic cause of FTLD.

15-20% of familial FTLD results from mutations in the MAPT gene on chromosome 17q21, encoding the microtubule associated protein tau. All cases with pathogenic MAPT mutations demonstrate prominent tau pathology. Interestingly, there are numerous families with autosomal dominant FTLD-U with linkage to chromosome 17q21 (MAPT region), in which no pathogenic MAPT mutations have been identified. It has been shown that this disease results from null-mutations of PGRN demonstrating there are 2 different genes for FTLD on chromosome 17q21.

It has also been established that Paget's disease with Inclusion Body Myopathy and FTD is caused by mutations in the VCP gene on chr9p; it is currently unclear to what extent, if any, this gene contributes to prototypical FTLD (i.e. without Paget's disease and Inclusion Body Myopathy).

There have also been reports of linkage to chr17q24 chr9p+q in pedigrees with FTD+MND. However, there have been no reports of other families linked to these regions, and the mutant genes have yet to be identified.

A recent genome-wide association study (Shatunov et al (2010) The Lancet; published on-line 31 Aug. 2010) highlighted that a disease loci for MND/ALS and FTLD (particularly FTD+MND/ALS) can be found on chromosome 9p21. However the authors were unable to identify any defective gene, or specific mutation at this location. Furthermore, despite an international effort no other authors have, to date, been able to provide any further insight on any defect at chromosome 9p21.

FTLD is the second most common form of dementia in individuals under the age of 65 where approximately half of all patients with FTLD present with a family history of a similar disorder indicating a significant genetic contribution to the etiology of this disease. MND/ALS is also a major problem with a significant genetic contribution to the etiology of the disease. Most existing methods of diagnosis for FTLD and MND/ALS are based on a combination of neuropsychological test results, brain imaging studies, and physical findings. Accordingly there remains a clear need for developing further methods of diagnosing FTLD and MND as well as assessing the likelihood that a subject will develop these disorders. Furthermore, at present there is no effective treatments for FTLD or MND and there is also a clear need to develop such therapies.

The limitations of sensitivity and reliability of existing assays mean that patients with an increased risk of developing neurodegenerative disease, or patients in the early stages of the disease are not necessarily identified using existing tests. The inability to identify such patients may mean that opportunities for therapeutic intervention prior to the appearance of debilitating symptoms of disease are lost. It will be appreciated that a prognostic test, and also diagnostic tests for early disease, are ideally performed before any major symptoms or anatomical changes in the brain may be detected.

In view of the above, the inventors endeavoured to develop a prognostic and diagnostic test for neurodegenerative disease by testing samples from control subjects and subjects with neurodegenerative disease.

The chromosome 9p21 locus (referred to herein as the c9FTD/ALS locus) contains one of the last major unidentified autosomal dominant genes underlying a common neurodegenerative disease. The inventors therefore undertook further studies of the c9FTD/ALS locus The inventors have established that a founder haplotype is present in the majority of cases linked to chromosome 9p21, and that this risk haplotype accounts for more than one third of familial MND/ALS cases in the Finnish population. The haplotype covers three known genes, MOBKL2b, IFNK and C9orf72.

After a significant amount of inventive endeavour the inventors were surprised to identify mutations of the C9orf72 gene in a very high proportion of subjects with a neurodegenerative disease (e.g. FTLD and/or MND/ALS).

The C9orf72 gene (HGNC ID: 28337) is known as a putative gene located at chromosome 9p21.2. However, to date, nothing has been reported about its function and the putative C9orf72 protein has little homology to known proteins.

Human C9orf72 genomic DNA sequence can be located from a number of publicly available databases. The NCBI database illustrates that the gene is located within 9:27,542,474 . . . 27,577,962.

Unless stated otherwise, when we refer to coordinates on chromosome 9 this is taken from UCSChg19/NCBI37 assembly (+ve strand).

The gene has two transcripts. NM_018325.2 represents a 3233 bp mRNA and is known as variant 1. It encodes isoform a of the C9orf72 protein which is a 481aa protein (NP_060795). NM_145005.4 represents a 1879 bp mRNA and is known as variant 2. It encodes isoform b of the C9orf72 protein which is a 222aa protein (NP_659442.2)

Diagnostic and Prognostic Tests Involving Detection of C9orf72 Gene Mutants

According to a first aspect of the invention there is provided a method of assessing whether a subject has or is likely to develop a Frontotemporal lobar degeneration (FTLD) comprising determining whether the subject has a mutation in the C9orf72 gene wherein said mutation prevents or disrupts C9orf72 expression relative to expression in a reference from subjects without FTLD or the mutation.

The method of the first aspect of the invention includes determining whether a subject has a mutation in the C9orf72 gene which disrupts or prevents C9orf72 expression. If the subject has such a mutation in the gene, this indicates that a subject has or is likely to develop dementia.

By "C9orf72 gene" we include the nucleic acid sequences set out above that encode the C9orf72 polypeptide or any fragment of that sequence. This can be genomic DNA sequence, mRNA sequence and cDNA sequence. C9orf72 gene nucleic acid sequences include the untranslated regions extending both upstream of the transcription start site of C9orf72 mRNA and downstream of the transcription termination site of C9orf72 mRNA by, for example, 5 Kb. C9orf72 gene nucleic acid sequences may include all exon and intron sequences. We also include polymorphisms or variations in that nucleotide sequence that are naturally found between individuals of different ethnic backgrounds or from different geographical areas and which do not affect the function of the gene. By "C9orf72 gene" we also include "regulatory elements", including the 5' and 3' of the gene which is involved in regulating gene transcription. For instance, transcription factor binding sequences, the TATA box, the 5' promoter and 5' and 3' untranslated regions (UTRs). This definition also encompasses the DNA 5' of the first codon of the first exon of C9orf72. At least some of this sequence information is provided in the accompanying description and figures.

A mutant C9orf72 nucleic acid is any C9orf72 nucleic acid containing a mutation as compared to a wild type C9orf72 nucleic acid. For example, a mutant human C9orf72 nucleic acid can be a nucleic acid having the nucleotide sequence of SEQ ID No. 1 having at least one mutation. By "mutation" as used herein with respect to nucleic acid, we include insertions of one or more nucleotides, deletions of one or more nucleotides, nucleotide substitutions, and combinations thereof, including mutations that occur in coding and non-coding regions (e.g., exons, introns, untranslated sequences, sequences upstream of the transcription start site of C9orf72 mRNA, and sequences downstream of the transcription termination site of C9orf72 mRNA).

The inventors have noted that the mutations the have identified result in a reduction in the expression of active C9orf72 or result in the abolition of C9orf72 expression. It will therefore be appreciated that the invention encompasses any mutation which represents a C9orf72 gene knock-out.

It is preferred that mutations according to the invention are insertion mutations which either cause a shift in the reading frame of the gene and therefore disrupt C9orf72 expression or result in the expression of a mutant protein which has reduced or more preferably, no C9orf72 activity.

It is also preferred that mutations according to the invention are mutations of intron 1 of the C9orf72 gene which either cause a shift in the reading frame of the gene and therefore disrupt C9orf72 expression or result in the expression of a mutant protein which has reduced, or more preferably no, C9orf72 activity.

It is preferred that the mutation according to the invention is found within the region of intron 1 of the C9orf72 gene which is transcribed with variant 2 (encoding isoform b of C9orf72) but not transcribed with variant 1 (encoding isoform a of C9orf72).

It is more preferred that mutations according to the invention are insertion mutations of intron 1 of the C9orf72 gene which either cause a shift in the reading frame of the gene and therefore disrupts C9orf72 expression or results in the expression of a mutant protein which has reduced or more preferably, no C9orf72 activity. It is preferred that the insertion is smaller than a decamer (e.g. a 9, 8, 7, 6 or 5 nucleic acid insertion).

It is even more preferred that the mutation is an insertion of a repeating nucleic acid motif in the C9orf72 gene and most preferably within intron 1. The insertion may be a repeat of any nucleic motif repeat. The motif may be a monomer, dimer, trimer, tetramer, pentamer, hexamer of nucleic acids or even larger. Preferably the motif is a hexamer. The motif may be a motif that may not be found in the wild type gene and may be present as 2, 3, 4, 5, 10, 20, 30, 50 or more repeats. However it is preferred that the repeat is a repeat of a motif that is already present in the wild type gene but is present as 2, 3, 4, 5, 10, 20, 30, 50 or more times than found in the wild type gene. The inventors have found, as explained below, that the number of such repeats can provide prognostic and diagnostic insight for a clinician and it is an important feature of the invention that the method may be adapted to detect how many repeats are inserted in to the C9orf72 gene.

It is more preferred that the mutation is the insertion of a GGCCCC (as shown in SEQ ID No. 1) hexanucleotide repeats, or an expansion of the number of such repeats found in the wild-type, in the first intron of the C9orf72 gene. It will be appreciated that this hexanucleotide will correspond to GGGGCC on the opposite strand. We therefore refer to the hexanucleotide repeat as GGCCCC or CCGGGG depending on the double helix strand worked on by the inventors.

It is most preferred that the mutation is a repeat of GGCCCC which is found starting at position 27,573,527 (coordinate taken from UCSChg19/NCBI37 assembly +ve strand)) in intron 1 of the C9orf72 gene and wherein the mutation is transcribed with the variant 2 mRNA (encoding isoform b of C9orf72) but not transcribed with the variant 1 mRNA (encoding isoform a of C9orf72).

The inventors have found that in control samples (i.e. subjects without FTLD or MND/ALS or a family history of these conditions) that there may between 0 and about 25 repeats of GGCCCC which is found starting at position 27,573,527 of chromosome 9. However on average they have found that there are 2 or 3 repeats of GGCCCC. For instance, there are three repeats (9:27573527 . . . 27573544=18 bp) in the C9orf72 gene found on the NCBI database.

In contrast the inventors were surprised to find (see Example 1) that subjects with neurodegenerative disease typically have 10, 20, 30, 50, 70, 100, 500, 600, 700, 1,000 or more of the GGCCCC repeats starting at position 27,573,527 of chromosome 9.

Some subjects with FTLD (or predisposed to develop FTLD) may have 20-100 repeats, 25-75 repeats or 30-71 repeats. Some subjects may have an average of about 50-60 (e.g. 53) GGCCC repeats. It has been noted that neurodegenerative disease is particularly associated with repeats over 25.

However the inventors have remarkably found that samples from subjects suffering from, or predisposed to develop, a neurodegenerative disease usually have significantly greater numbers of GGCCC repeats than found in the wild type. Accordingly it is most preferred that the methods of the invention are used to identify subjects with an expansion of greater than 100 repeats and preferably greater than about 500 repeats. For instance subjects may have repeats of more than 500, 600, 700 or even more than 1,000 of the hexanucleotide repeats in intron 1 of the C9orf72 gene. For instance there may be 600-4,000+ repeats or about 700-3800 repeats.

The inventors have identified a genetic linkage between the mutated C9orf72 gene and neurodegenerative disease. The inventors have established that the mutated C9orf72 gene may be used as a prognostic and diagnostic marker for disorders that are at least partially characterised by neurodegeneration (e.g. FTLD or MND/ALS).

The method of the first aspect of the invention may preferably be applied to testing for a wide range of dementias, including those associated with Alzheimer's disease, Lewy Body Dementia and Parkinson's disease but is particularly useful for testing in connection with frontotemporal lobar degeneration (FTLD). The syndrome of FTLD encompasses the clinical subgroups of FTD, FTD with motor neuron disease (MND or ALS), semantic dementia and primary progressive aphasia, and is characterized by changes in behaviour, personality and language with relative preservation of memory and perception The method of the first aspect of the invention may also be preferably applied to testing for MND/ALS (with or without dementia).

While it can be appreciated that the method of the invention can be applied to animal subjects of veterinary interest, it is preferred that the subject to be tested is a human subject.

Conducting the Diagnostic Test on Nucleic Acid Samples

The method according to the first aspect of the present invention is an in vitro method and can be performed on a sample containing nucleic acid derived from a subject.

The method of the first aspect of the invention is particularly suitable for being carried out on genomic DNA, particularly on isolated genomic DNA. Such genomic DNA may be isolated from blood or tissue samples (e.g. hair, oral buccal swabs, nail or skin, blood, plasma, bronchoalveolar lavage fluid, saliva, sputum, cheek-swab or other body fluid or tissue), or from other suitable sources, using conventional methods. The nucleic acid containing sample that is to be analysed can either be a treated or untreated biological sample isolated from the individual. A treated sample, may be for example, one in which the nucleic acid contained in the original biological sample has been isolated or purified from other components in the sample (tissues, cells, proteins etc), or one where the nucleic acid in the original sample has first been amplified, for example by polymerase chain reaction (PCR). Thus, it will be appreciated that the sample may equally be a nucleic acid sequence corresponding to the sequence in the sample, that is to say that all or a part of the region in the sample nucleic acid may firstly be amplified using any convenient technique e.g. PCR, before analysis of allelic variation.

The identification of a C9orf72 gene mutation (e.g., one or more of the mutations listed above) in an allele can be used to determine whether a subject has or is likely to develop FTLD. Such a method may be performed when a subject has already exhibited clinical symptoms of FTLD (i.e. as an adjuvant to existing techniques for diagnosing such neurological disorders). Alternatively, the method may be performed as a means of assessing whether the subject has a predisposition towards developing FTLD (i.e. for the purposes of genetic counseling of subject—particularly those with a family history of FTLD). This enables a medical practitioner to take appropriate action to prevent or lessen the likelihood of onset of the disease or disorder or to allow appropriate treatment of the disease or disorder.

Various different approaches can be used to determine whether a subject has a mutation in the C9orf72 gene. These include haplotype analysis of genomic DNA of the subject; determining the nucleic acid sequence of the C9orf72 gene; and determining the nucleic acid sequence of mRNA encoding the C9orf72 polypeptide.

A preferred embodiment of the first aspect of the invention may include the step of determining whether the subject has a mutation in the C9orf72 gene by genotyping the C9orf72 gene.

Methods of genotypic analysis are well known to those skilled in the art. The genotype may preferably be determined by testing a sample from the subject. Preferably the sample contains genomic DNA and most preferably the DNA comprises a nucleic acid molecule according to the second aspect of the invention (see above). Methods of providing samples of genomic DNA from a subject are routinely performed by the skilled person.

The nucleic acid sequence for the C9orf72 gene is provided herein and as part of the database entries given above. This information can be used to design materials, such as oligonucleotide primers or probes specific for each allele that can be used when determining the genotype of the C9orf72 gene of a subject. The design of such oligonucleotide primers is routine in the art and can be performed by the skilled person with reference to the information provided herein without any inventive contribution. If required, the primer(s) or probe(s) may be labelled to facilitate detection.

Preferred primers for use in PCR based embodiments of the first aspect of the invention are listed in 1.2.8 of Example 1.

Techniques that may be used to detect mutations include:—(1) Sequence Specific Oligonucleotide Hybridization (SSO) (involving dot or slot blotting of amplified DNA molecules comprising the polymorphic region; hybridisation with labelled probes which are designed to be specific for each polymorphic variant; and detection of said labels); and (2) Heteroduplex and single-stranded conformation polymorphism (SSCP) Analysis (involving analysis of electrophoresis band patterns of denatured amplified DNA molecules comprising the polymorphic region).

Reference Strand mediated Conformational Analysis (RSCA) can also be used for C9orf72 gene genotyping. A PCR reaction is performed on a sample of DNA isolated from a subject using primers that flank a region of the C9orf72 gene. The amplified product is then hybridized with fluorescent-labeled reference DNA molecules at a temperature that permits annealing to occur, even when mismatches are present. Mismatches between the reference strand and the sample DNA result in the formation of bulges or "bubbles" in the heteroduplex that is formed. The number and location of the bulges give the heteroduplex a unique mobility on a polyacrylamide gel, and can be used to determine whether there is a mutation in the C9orf72 gene.

A further method is sequence based typing (SBT). SBT combines a low-resolution SSP-PCR reaction followed by high resolution allele typing using automated DNA sequencing. In summary, DNA isolated from a subject is used as a template for a PCR reaction that amplifies a region of the C9orf72 gene (e.g. intron 1) to create a primary amplification product. That product is then purified to remove excess reaction reagents, though there are single-tube reactions available in which this purification step is not required. The primary amplification product is then used as a template for sequencing reactions. Once complete, the sequence reactions are analysed by a sequencer, and the products analysed to determine whether there is a mutation in the C9orf72 gene.

Where PCR amplification is required as part of the method of genotyping, PCR primers may be designed such that they are suitable for amplifying a region of the C9orf72 gene. The design of suitable PCR primers is a routine laboratory technique.

Quantitative PCR represents a preferred method of determining mutations, and especially the hexanucleotide insertion mutation, in the C9orf72 gene Southern Blotting A preferred method of determining mutations in the C9orf72 gene is to employ Southern blotting. Southern blotting is a technique that is well known in the art and it may be performed as set out in Sambrook et al (1989). Molecular cloning, a laboratory manual, $2^{nd}$ edition, Cold Spring Harbor Press, Cold Spring Harbor, New York).

Southern blotting represents a preferred procedure for detecting mutations in the C9orf72 gene and a preferred protocol is provided in Example 2.

mRNA Analysis

A further embodiment of the first aspect of the invention is wherein the method comprises determining the nucleic acid sequence of mRNA encoding the C9orf72 polypeptide.

Methods of isolating mRNA molecules from a sample are routine in the art and well known to the skilled person. Once isolated, the nucleotide sequence of the mRNA molecule can be determined, preferably from a cDNA sample prepared from mRNA isolated from the subject. The sequence of cDNA molecules can be determined according to the genotyping methods set out above.

The mRNA with NCBI reference number NM_018325.2 (C9orf72 transcript variant 1) which encodes LOC203228 isoform a (NP_060795.1) may be examined according to this embodiment of the invention although it is preferred that the mRNA with NCBI reference number NM_145005.4 (C9orf72 transcript variant 2) which encodes LOC203228 isoform b (NP_659442.2) is examined.

Most preferred methods of detecting the mutation in nucleic acid samples derived from c9p21 is to employ repeat-primed PCR as outlined in 1.2.3 of Example 1 or Southern Blotting as outlined in Example 2.

Isolated DNA Molecules

The discovery by the inventors that intron 1 of the C9orf72 gene may comprise a mutation that may be linked to neurodegenerative disease represents an important development in the art. It will be appreciated that the identification of the mutation made it desirable to isolate a DNA molecule comprising intron 1 or a substantial portion thereof. The inventors proceeded to use various techniques (including restriction enzymes) to isolate such a molecule and according to a second aspect of the invention this provided an isolated nucleic acid molecule substantially comprising intron 1 of the C9orf72 gene.

The isolated nucleic acid molecule may be DNA or RNA and may comprise intron 1 of the C9orf72 gene and about 3,000 bp 5' and 3' of the intron; preferably it comprises intron 1 of the C9orf72 gene with about 1,000 bp 5' and 3' of the intron; more preferably it comprises intron 1 of the C9orf72 gene with up to about 250 bp 5' and 3' of the intron; and most preferably it comprises intron 1 of the C9orf72 gene or a substantial part thereof. By a "substantial part thereof" we mean a fragment of the intron that comprises at least position 9:27573527 with "n" repeats of the GGCCC hexanucleotide repeat starting therefrom.

Methods for generating a fragment of genomic DNA are well known to the art. SEQ ID NO. 1 represents a 3794 bp nucleic acid fragment of genomic DNA from chromosome 9p21.2 that is generated by treatment with the restriction enzyme Hind III and comprises 9:27572920 . . . 27576713. This nucleic acid molecule represents the wild type gene and comprises three GGCCCC repeats (underlined). SEQ ID NO. 1 represents a preferred molecule according to the second aspect of the invention.

```
                                              SEQ ID No. 1
AGCTTGG

GCTGAAATTGTGCAGGCGTCTCCACACCCCCATCTCATCCCGCATGATCT

CCTCGCCGGCAGGGACCGTCTCGGGTTCCTAGCGAACCCCGACTTGGTCC

GCAGAAGCCGCGCGCCGCCCACCCTCCGGCCTTCCCCCAGGCGAGGCCTC
```

-continued

```
TCAGTACCCGAGGCTCCCTTTTCTCGAGCCCGCAGCGGCAGCGCTCCCAG
CGGGTCCCCGGGAAGGAGACAGCTCGGGTACTGAGGGCGGGAAAGCAAGG
AAGAGGCCAGATCCCCATCCCTTGTCCCTGCGCCGCCGCCGCCGCCGCCG
CCGCCGGGAAGCCCGGGGCCCGGATGCAGGCAATTCCACCAGTCGCTAGA
GGCGAAAGCCCGACACCCAGCTTCGGTCAGAGAAATGAGAGGGAAAGTAA
AAATGCGTCGAGCTCTGAGGAGAGCCCCCGCTTCTACCCGCGCCTCTTCC
CGGCAGCCGAACCCCAAACAGCCACCCGCCAGGATGCCGCCTCCTCACTC
ACCCACTCGCCACCGCCTGCGCCTCCGCCGCCGCGGGCGCAGGCACCGCA
ACCGCAGCCCCGCCCCGGGCCCGCCCCGGGCCCGCCCCGACCACGCCCC
GGCCCCGGCCCCGGCCCCCTAGCGCGCGACTCCTGAGTTCCAGAGCTTGC
TACAGGCTGCGGTTGTTTCCCTCCTTGTTTTCTTCTGGTTAATCTTTATC
AGGTCTTTTCTTGTTCACCCTCAGCGAGTACTGTGAGAGCAAGTAGTGGG
GAGAGAGGGTGGGAAAAACAAAAACACACACCTCCTAAACCCACACCTGC
TCTTGCTAGACCCCGCCCCAAAAGAGAAGCAACCGGGCAGCAGGGACGG
CTGACACACCAAGCGTCATCTTTTACGTGGGCGGAACTTGTCGCTGTTTG
ACGCACCTCTCTTTCCTAGCGGGACACCGTAGGTTACGTCTGTCTGTTTT
CTATGTGCGATGACGTTTTCTCACGAGGCTAGCGAAATGGGGCGGGCAA
CTTGTCCTGTTCTTTTATCTTAAGACCCGCTCTGGAGGAGCGTTGGCGCA
ATAGCGTGTGCGAACCTTAATAGGGGAGGCTGCTGGATCTGGAGAAAGTG
AAGACGATTTCGTGGTTTTGAATGGTTTTGTTTGTGCTTGGTAGGCAGTG
GGCGCTCAACACATAATTGGTGGATGAAATTTTGTTTTTACCGTAAGACA
CTGTTAAGTGCATTCAAAACTCCACTGCAAACCCTGGTAGGGGACAGCTC
CGGCACTGCGGGCGGGAATCCCACGGTCCCCTGCAAAGTCATCGCAATTT
TGCCTTTACATGTAAGAATTCTCTCAAGCATGATTTTCACACTGGGGAAT
GTCATTTTTGCTAGTTGCAATATGTGGATGAGTTGTTTTTTTTTAACTTT
TGAAAAACGTACCATTCTGTTTGATGTGTAAAAAACACAAAGATTTTTGA
AACCTTGCGTCTTTTGGTCTGCAGGTGTATAGATTCCACTTACTACAGAT
GAGTAGCATTTACACCACTCAGATGTGTAAAAAAACAAAGGTTTTTTAAA
CTGTGTGCCTTTTGATCTGCAAGTGTGAGATGGCACTTACTACAGTGAGT
AGCATTTAATCTTTTTCATCACTAAAAATCACACAGAACGTTTTAATCAT
TCACCGAGGAAGAAAGGGAGGAATAAATACACAAAATGGCTCTCAACGTC
TACACCTTCTGCAGAAACAGACCCTTTTCCTACTGTTCTATGCTTTGTGA
AAGTTGATCATACAAATTGGGTCATTCTTTTTATACCCAACTAAAATAGT
GGGGGTAGGGGGTAGAAAAGCACTTAGGACAAATGACACTGCTCCCACAG
TGTAATTCTCTCCAAGTCCAGCTGCTGCAACTGCCCGTTGTGACCTGAGA
CCAGTTTTATCTAATAGTTGCTAAAATGACCTGCTGCAGCTCTAATTTTA
TCTACCACCATCACTCACCAGTTGAAACTCACCAGCTCCTCAGATCCTTA
ATAGTGCCAATGAATTTTCTCAAAGAGCACTATGTAACATTTCTCTTTTT
TAACAAAACCTCCCCCTTTTCTTTGTTGTGTGGATATACCGAAGACCATC
TGATCTACATGTATGCCCTAATTGCAATTCTTTCTTCCCAAATAAATCAC
TTAATTTAGAGATTCATCTCTGTATTTTTATTTTGACTGACAGCTTATAA
CAAGTAGCTAGCATTTACCAAGTTTCTACACTGAGTTGTACTTCACTTAT
ACGTGGAATTAAAAAACAACTGAATTTATAGAAACAGAGTAGACCCTTGG
TTGGGGGGCTTGGGGGGAAAGAAAATTGTAGGGTAGGGTACAAAGTTGCA
GTTACGTCTAATACATCTAGAGATTTAATGTACAACATGAGGACTAGCGT
TAATAATTGTGTTAGTCCATTCTTACACTGCTATAAAGAAATAACTGAAA
CTGGGTAATTTATAAAGAAAAGTTTAATGGCTCACAGTTCTGCAGGCTGT
ACAAGAAGCATGGCTGGATCAGCTTCTGGGCAGGCCATAGGGAACTTAAA
ATCATGATGGAAGGCATAGGGAGACCCCAGACTTCACATGGCAGGAACTG
GGGGAAGAGAGAAATGGGAGGTGCTACATACGTTTAAACAACTAGATCTT
GTCAGAACTCACTATATAGTACCAAGAGGGGACTGTACAAAACCATTAGA
AGCCACCCCATAATCCACTCACCTCCCACCAGGCCCAACCTCCAACACTG
GGGATTACAGTTGAACATGAGATTTGGGTGGGACAGAGATCCAAACCAT
GTTATTCCAACTCTGGCCCCTCCCAAATCTAATGTCCTTCTCATATTGCA
AAATACTGTCGTGCCTTACCAACAGTTCCCCAAAGTCTTAACTCGATCCA
GCATTCATTCAAAAGTCCAAAGTCCCAAGTCTCACCTGAGACGAAGCTAG
TCCCTTCTACCTATGAACCTGTAAAATCAAAAACAAGGTAATTGCTTCAA
AGATACAATGGGGGTATAGGCATTGGGCAGATACTGCCATTCCGAAAGGG
AGAAATCTGCCAAAAGAAAGAGGCTATAGGGCCCCATTGCAAGTCTGAAA
GCCAGCCGGGCAGTCATTAAATGTTAAAGCTCTGAAATAATCTCCTTTGA
CTCACACCCAGGGAACACTGATGCAATGAGTGGGCTCCCAAAACCTTGGG
CAGAACCACCCCTGTGGTTTTCCAGGGTTCATCTCCCACAGCTGCTCTCA
TGGGCTAGCATTGAGTGCTTGCAGCTTTTCCAGGCTGCAGGGTGCAAGTT
GTTGGTGGATCTACCATTCTGGGGTCTGGAGGACGGTGGCTGTCTTGTCA
TAGCTCTGCTAGGCAGTGCCCCAGGGGACTCTCTGTGGGGGCTGCAACCC
CACATTTCTTCTCCTTGCTTCCCTAGTAGATGTTCTCCATGAGGATTCCA
CCCCAGTAACAGGCTTCTGTCTGGACATCCAGGCTTTTTCATACATCCTC
TAAAATCTAGGCAGAGCTTCTTAAGCCTCAACTCTTGCATTATGTGCGCC
CGCCGGCTTCACAGCTTATGGAAGCCACCAAGGCTTATGCCTGGCACCCT
GTGAAGCAGCAGCCTGAACTGTATTCTTACTGGTGAAAGTTATCTGAGTT
ACCAGCTGCAAATCCATGTGGGTCTGCAGCAACCTCAATTCTTGCCTCCT
CAGAAGAAAGAATTTGACCAAGAGGCATAAGGCAGAAAAAGAGACTGCGA
CAAGTTTCAGAGCAGGAGTAAAAGTTTATTAAAAAGCT.
```

Other preferred nucleic acid molecules according to the second aspect of the inventions are: a genomic DNA fragment of 10,018 bp (9:27568527 ... 27578544) and a 3,387 bp BpuEI fragment (9:27570847 ... 27574233=3387 bp)

Diagnostic and Prognostic Tests Involving Detection of C9orf72 Protein Levels or Detection of C9orf72 Protein Activity The inventors have established that the mutations in the C9orf72 gene that are linked to FTD and/or MND result in either a reduction or prevention of C9orf72 expression; or the expression of a non-functional C9orf72 mutant protein.

According to a third aspect of the invention there is provided an in vitro method for identifying a subject predisposed to, or suffering from, a neurodegenerative disease, the method comprising examining C9orf72 protein levels in a sample from a test subject and comparing those C9orf72 protein levels with a reference derived from an individual who does not suffer from a neurodegenerative disease, wherein a decreased concentration of active C9orf72 protein or the presence of a mutant C9orf72 protein in the sample from the test subject suggests that the subject is suffering from a neurodegenerative disease or is predisposed to developing a neurodegenerative disease.

Human C9orf72 protein has been assigned UniProtKB/Swiss-Prot accession number Q96LT7 and named as hypothetical protein LOC203228. It exists in two isoforms. Isoform a comprises approximately 481 and isoform b comprises about 222 amino acids. The protein The sequences for human C9orf72 protein can be located from a number of different databases. For instance NCBI reference NP_060795.1 represents isoform a and NP_659442.2 represents isoform b.

Isoform a of C9orf72 has the following amino acid sequence:

```
                                              (SEQ ID NO: 2)
         10         20         30         40
MSTLCPPPSP AVAKTEIALS GKSPLLAATF AYWDNILGPR 50         60         70         80
VRHIWAPKTE QVLLSDGEIT FLANHTLNGE ILRNAESGAI 90        100        110        120
DVKFFVLSEK GVIIVSLIFD GNWNGDRSTY GLSIILPQTE 130        140        150        160
LSFYLPLHRV CVDRLTHIIR KGRIWMHKER QENVQKIILE 170        180        190        200
GTERMEDQGQ SIIPMLTGEV IPVMELLSSM KSHSVPEEID 210        220        230        240
IADTVLNDDD IGDSCHEGFL LNAISSHLQT CGCSVVVGSS 250        260        270        280
AEKVNKIVRT LCLFLTPAER KCSRLCEAES SFKYESGLFV 290        300        310        320
QGLLKDSTGS FVLPFRQVMY APYPTTHIDV DVNTVKQMPP 330        340        350        360
CHEHIYNQRR YMRSELTAFW RATSEEDMAQ DTIIYTDESF 370        380        390        400
TPDLNIFQDV LHRDTLVKAF LDQVFQLKPG LSLRSTFLAQ 410        420        430        440
FLLVLHRKAL TLIKYIEDDT QKGKKPFKSL RNLKIDLDLT 450        460        470        480
AEGDLNIIMA LAEKIKPGLH SFIFGRPFYT SVQERDVLMT

F
```

Isoform b of C9orf72 is a truncation a and has the following amino acid sequence:

```
                                              (SEQ ID NO: 3)
         10         20         30         40
MSTLCPPPSP AVAKTEIALS GKSPLLAATF AYWDNILGPR 50         60         70         80
VRHIWAPKTE QVLLSDGEIT FLANHTLNGE ILRNAESGAI 90        100        110        120
DVKFFVLSEK GVIIVSLIFD GNWNGDRSTY GLSIILPQTE 130        140        150        160
LSFYLPLHRV CVDRLTHIIR KGRIWMHKER QENVQKIILE 170        180        190        200
GTERMEDQGQ SIIPMLTGEV IPVMELLSSM KSHSVPEEID 210        220        230        240
IADTVLNDDD IGDSCHEGFL LN
```

To be considered a C9orf72 polypeptide as defined herein, a polypeptide may have at least 50%, 60% to 70% and more preferably 70% to 80%, 80 to 90%, 90 to 95%, 96%, 97%, 98%, 99% or more sequence identity with a C9orf72 polypeptide sequences provided herein, for example as given in one of the listed accession numbers above or that of SEQ ID NO: 2 or 3.

A "fragment" of the C9orf72 polypeptide can be considered to be an C9orf72 polypeptide that may comprise, for example, 50%, 60%, 70%, 80%, 90%, 95%, 96%, 97%, 98%, 99% or more or of the polypeptide sequence of full length 222 or 481 amino acid polypeptide.

A "variant" will have at least 50% (preferably 60%, 70%, 80%, 90%, 95%, 86%, 97%, 98%, 99% or more) sequence identity with a C9orf72 polypeptide as described herein. The percentage identity may be calculated by reference to a region of at least 50 amino acids (preferably at least 60, 75, or 100) of the candidate variant molecule, allowing gaps of up to 5%. By "variants" we also include insertions, deletions and substitutions, either conservative or non-conservative. In particular we include variants of the polypeptide where such changes do not substantially alter the protein activity or ability to bind to particular binding partners, as appropriate.

Due to the degeneracy of the genetic code, it is clear that any nucleic acid sequence could be varied or changed without substantially affecting the sequence of the protein encoded thereby, to provide a functional variant thereof. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. Therefore by "conservative substitutions" is intended to include combinations such as Gly, Ala; Val, Ile, Leu; Asp, Glu; Asn, Gln; Ser, Thr; Lys, Arg; and Phe, Tyr.

We also include homologues of C9orf72 polypeptide present in other species. These polypeptide are also included within the scope of the term "C9orf72" when referred to herein.

The three-letter or one letter amino acid code of the IUPAC-TUB Biochemical Nomenclature Commission is used herein.

Calculation of percentage identities between different amino acid/polypeptide/nucleic acid sequences may be carried out as follows. A multiple alignment is first generated by the ClustalX program (pairwise parameters: gap opening 10.0, gap extension 0.1, protein matrix Gonnet 250, DNA matrix IUB; multiple parameters: gap opening 10.0, gap extension 0.2, delay divergent sequences 30%. DNA transition weight 0.5, negative matrix off, protein matrix gonnet series, DNA weight IUB; Protein gap parameters, residue-specific penalties on, hydrophilic penalties on, hydrophilic residues GPSNDQERK, gap separation distance 4, end gap separation off). The percentage identity is then calculated from the multiple alignment as (N/T)*100, where N is the number of positions at which the two sequences share an identical residue, and T is the total number of positions compared. Alternatively, percentage identity can be calculated as (N/S)*100 where S is the length of the shorter sequence being compared. The amino acid/polypeptide/nucleic acid sequences may be synthesized de novo, or may be native amino acid/polypeptide/nucleic acid sequence, or a derivative thereof.

A "mutant C9orf72 polypeptide" is any C9orf72 polypeptide containing an alteration to the amino acid sequence as compared to a wild type C9orf72 polypeptide. For example, a mutant human C9orf72 polypeptide can be a polypeptide having the amino acid sequence above having at least one alteration; for example this could be a substitution of one or more amino acid residues with other amino acid residues; this could be an insertion of one or more amino acid residues; this could be a deletion of one or more amino acid residues, and possibly a truncation of a large region of the C9orf72 polypeptide. It is preferred that the mutant C9orf72 polypeptide is encoded by the mutant nucleic acid sequences discussed above.

It will be appreciated that determining whether a sample contains a certain level of C9orf72 polypeptide may be diagnostic of a neurodegenerative disease or it may be used by a clinician as an aid in reaching a diagnosis. Levels of C9orf72 polypeptide may be monitored over time in a patient that has developed a neurodegenerative disease to assess how the disease develops. In most instances, a decrease in C9orf72 polypeptide levels over time will suggest to the clinician that the health of the subject is deteriorating. Accordingly the method has prognostic value in connection with subjects that already suffer from the disease.

The methods of both the first and third aspects of the invention may also be used for presymptomatic screening of a subject who may be in a risk group for developing a neurodegenerative disease, e.g. a patient having a family history of FTD and/or MND. Hence the methods of the invention may also be used to screen individuals who are asymptomatic. Lowered C9orf72 polypeptide levels may then lead a clinician to recommend prophylactic treatment or even just life style changes.

By "lowered concentration of C9orf72 polypeptide in the bodily sample" we mean that the level of polypeptide which can be considered to be an indicator of a neurodegenerative disease may be, for example, at least 1½ fold lower, or it may be at least 2-fold, or 3-fold, 5-fold, 7-fold, 10-fold, 50-fold or even lower, in the sample than the level of C9orf72 polypeptide in a sample taken from an individual who is not genetically predisposed to, or suffering from, a neurodegenerative disease. It is preferred that levels of isoform b are measured. The inventors have found that the GGCCCC repeat mutation in intron 1 of C9orf72 has the effect of reducing the expression of isoform b and thereby lowering concentration of C9orf72 polypeptide isoform b in the bodily sample.

Samples used according to the method of the third aspect of the invention may be any suitable body tissue (e.g. a tissue biopsy) or body fluid (e.g. central spinal fluid). It is preferred that the sample is a peripheral body fluid sample. By the term "peripheral body fluid sample", we mean any body fluid that lies outside the central nervous system. For example the sample may be urine, sputum or lymph. However, it is preferred that the body fluid is blood or derived therefrom. The method of the first aspect of the invention is most preferably performed on a sample of serum or plasma.

C9orf72 polypeptide is preferably measured or assayed in a blood sample. The blood sample may be venous or arterial. Blood samples may be assayed immediately. Alternatively, the blood may be stored in a fridge before the assay is conducted. Measurement may be made in whole blood. However, in preferred embodiments of the invention, the blood may be further processed before an assay is performed. For instance, an anticoagulant, such as heparin, citrate, EDTA, and others may be added. It is most preferred that the blood sample is centrifuged or filtered to prepare a plasma or serum fraction for further analysis. It is most preferred that the sample is plasma. The plasma may be used immediately after it has been separated from blood cells or, alternatively it may be refrigerated or frozen before assay.

C9orf72 polypeptide levels may be measured by a number of ways known to one skilled in the art. It will be appreciated that the polypeptide may be detected by labelling a compound having affinity for C9orf72 polypeptide. Antibodies, aptamers and the like may be labelled and used in such an assay.

C9orf72 polypeptide may be detected by non-immuno based assays. Such non-immuno based assays may utilise fluorometric or chemiluminescent labels. However, it is preferred that immunoassays are employed to detect C9orf72 polypeptide concentration in the sample. Examples of immunoassays include immunofluorescence techniques known to the skilled technician, immunohistochemistry, radioimmunoassay analyses and in particular enzyme-linked immunosorbant assay (ELISA).

Hence, a preferred method of measuring C9orf72 polypeptide comprises carrying out an ELISA on the sample. It may be required to first separate the proteins in the sample, for example, using isoelectric focussing before the ELISA step. As will be appreciated, such techniques are routine laboratory methods and are well known to the skilled person.

The methods of the third aspect of the invention may need a "reference sample". This would be the amount and/or activity of C9orf72 polypeptide in a sample of protein taken from a subject that does not have a neurodegenerative disease and preferably has no family history of developing such diseases.

The polypeptide sequence for C9orf72 is provided herein. This information can be used to design materials, such as antibodies or further specific binding molecules, that may be required for the methods set out below.

Methods of the third aspect of the invention are preferably employed to detect whether there is a decrease in wild type C9orf72 levels and/or activity. However the methods may be adapted to determine whether a subject has a mutant C9orf72 protein. This may be achieved by isolating then sequencing C9orf72 protein from a sample derived from that subject. Methods of purifying proteins are well known in the art and can be readily applied to the method of the invention. For example, a molecule that selectively binds to the C9orf72 protein, e.g. an antibody or a fragment of an antibody, can be used to purify the C9orf72 protein from the sample from the subject. Then, using well-known peptide sequencing methods, such as N-terminal sequencing, the amino acid sequence of the isolated protein can be determined and compared to that of the wild type protein. In a preferred embodiment, the presence of a mutant C9orf72 polypeptide in a sample can be detected using an antibody that selectively binds to a mutant C9orf72 polypeptide. Antibodies which can selectively bind to mutant C9orf72 polypeptides can be made, for example, using peptides that include amino acid sequences particular to that mutation (e.g. the hexanucleotide repeat).

Various procedures known within the art may be used for the production of polyclonal or monoclonal antibodies directed against a C9orf72 polypeptide or mutant C9orf72 polypeptide (see, for example, Antibodies: A Laboratory Manual, Harlow E, and Lane D, 1988, Cold Spring Harbor Laboratory Press, Cold Spring Harbor, N.Y., incorporated herein by reference), and are well known to those skilled in the art.

Screening assays to determine binding specificity of such an antibody are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6.

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982). Such methods include the use of hybridomas, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Anti-C9orf72 antibodies are known to the art. For example sc-138763 from Santa Cruz Biotechnology Inc.; HPA023873 from Sigma-Aldrich; or GTX119776 from GeneTex.

It will be appreciated that other antibody-like molecules may be used in the method of the inventions including, for example, antibody fragments or derivatives which retain their antigen-binding sites, synthetic antibody-like molecules such as single-chain Fv fragments (ScFv) and domain antibodies (dAbs), and other molecules with antibody-like antigen binding motifs.

Animal Model

A fourth aspect of the invention provides a non-human genetically modified animal having, or being predisposed to develop a neurodegenerative disease, wherein the animal has a mutation of the C9orf72 gene, or homolog thereof in the animal that is associated with the neurodegenerative disease.

The mutant C9orf72 gene may be as defined above.

As set out above, mutation of the C9orf72 gene is associated with neurodegenerative disease and particularly FTLD and MND/ALS. Animals with a decreased expression of wild type C9orf72 protein can be expected to be predisposed to developing neurodegenerative diseases (dementias, MND etc) and will also display the symptoms of such diseases. Such animals are therefore useful in methods for screening for potential therapeutic agents for preventing or treating neurodegenerative diseases and particularly dementias (such as FLD) and also MND/ALS.

The non-human animal may be any non-human animal, including non-human primates such as baboons, chimpanzees and gorillas, new and old world monkeys as well as other mammals such as cats, dogs, rodents, pigs or sheep, or other animals such as poultry, for example chickens, fish such as zebrafish, or amphibians such as frogs. However, it is preferred that the animal is a rodent such as a mouse, rat, hamster, guinea pig or squirrel. Preferably the animal is mouse.

By "neurodegenerative disease", "FTLD", "MND" and "FTD" we include those disorders discussed above in relation to the first aspect of the invention.

There are a number of different methods that can be employed to generate a non-human genetically modified animal according to this aspect of the invention. These will be discussed in turn below. Preferred methods include those in which the gene encoding the said polypeptide is altered or removed so as to produce little or none of said polypeptide. Other methods include inhibiting the transcription of the said gene or preventing any mRNA encoded by said gene from being translated due to the animal being genetically modified so as to have an agent which can modify said polypeptide transcription, translation and/or function.

Preferably, the methods set out below are employed to generate a non-human genetically modified animal according to this aspect of the invention in which the expression of wild type C9orf72 protein is reduced.

"Homologous recombination" is a technique well known to those skilled in the art. Animals in which an endogenous gene has been inactivated by homologous recombination are referred to as "knockout" animals. Hence this aspect of the invention includes wherein the C9orf72 gene is mutated by homologous recombination.

"Insertional mutagenesis" is also a term well known to those skilled in the art. Examples of such mutagenesis include transposon-tagging, homing endonuclease genes (HEGs). In such methods a region of DNA is introduced into a gene such that the controlling or coding region of the gene is disrupted. Such methods can be used to disrupt the C9orf72 gene. As a result the animal will no longer be able to synthesise C9orf72 polypeptide, i.e. there will be a reduction in the amount of this polypeptide. It is preferred that the insertion is a hexanucleotide repeat (e.g. GGCCCC) and the insertion is also preferably within intron 1 of the gene as discussed above.

Chemical or physical mutagenesis can also be used in the method of this aspect of the invention. Here, a gene is mutated by exposing the genome to a chemical mutagen, for example ethyl methylsulphate (EMS) or ethyl Nitrosurea (ENU), or a physical mutagen, for example X-rays. Such agents can act to alter the nucleotide sequence of a gene or, in the case of some physical mutagens, can rearrange the order of sequences in a gene. Practical methods of using chemical or physical mutagenesis in animals are well known to those skilled in the art. Such methods can be used to disrupt the C9orf72 gene. As a result the animal may no longer be able to synthesise C9orf72 polypeptide, i.e. there will be a reduction in the amount and/or function of this polypeptide.

Homologous recombination, insertional mutagenesis and chemical or physical mutagenesis can be used to generate a non-human animal which is heterozygous for the C9orf72 gene ($^{+/-}$). Such animals may be of particular use if the homozygous non-human animal has too severe a phenotype.

The non-human animal of this aspect of the invention could be genetically modified to include an antisense molecule or siRNA molecule that can affect the expression of the C9orf72.

Antisense oligonucleotides are single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise sequence-specific molecules which specifically bind double-stranded DNA via appropriate formation of major groove hydrogen bonds.

By binding to the target nucleic acid, the above oligonucleotides can inhibit the function of the target nucleic acid. This could, for example, be a result of blocking the transcription, processing, poly(A)addition, replication, translation, or promoting inhibitory mechanisms of the cells, such as promoting RNA degradations.

By "antisense" we also include all methods of RNA interference, which are regarded for the purposes of this invention as a type of antisense technology.

Human C9orf72 polypeptides and nucleotide sequences are set out above. A mouse homolog (Mouse symbol: 3110043O21Rik) and rat homolog (Rat Symbol: RGD1359108) have also been identified and it will be appreciated that mouse and rat models according to the invention will contain mutations of the respective species-specific genes.

Medical Treatments

According to a fifth aspect of the present invention, there is provided a C9orf72 protein or an active fragment thereof, an agent that promotes or mimics C9orf72 activity or a nucleic acid encoding C9orf72 for use as medicament for the prevention or treatment of neurodegenerative disease.

According to a sixth aspect of the invention there is provided a method of preventing or treating neurodegenerative disease comprising administering to a subject in need of such treatment a therapeutically effective quantity of C9orf72 protein or an active fragment thereof, an agent that promotes or mimics C9orf72 activity or a nucleic acid encoding C9orf72.

The inventors, as explained above and in the Example, have demonstrated that mutations of the C9orf72 gene that result in decreased C9orf72 protein expression is linked to a predisposition to developing neurodegenerative disease. This lead them to realise that proteins, agents and nucleic acids according to the fifth or sixth aspect of the invention or an agent that promotes or mimics C9orf72 activity protein are useful for preventing or treating neurodegenerative disease.

The proteins, agents and nucleic acids may be used in the treatment of FTLD and are particularly useful for treating a number of different dementias, preferably FLD. The proteins, agents and nucleic acids are also particularly useful for treating FLD associated with MND. The proteins, agents and nucleic acids are also particularly useful for treating MND/ALS irrespective of whether or not it is associated with FLD.

Examples of agents which may be used according to the fifth or sixth aspects of the invention include where the agent may bind to the C9orf72 protein and increase functional activity, e.g. antibodies and fragments and derivatives thereof (e.g. domain antibodies or Fabs). Alternatively the agent may increase C9orf72 protein activity by acting as an agonist at C9orf72 receptors. Alternatively the agent may activate enzymes or other molecules in the C9orf72 protein synthetic pathway. Alternatively the agent may bind to mRNA encoding C9orf72 protein in such a manner as to lead to an increase in that mRNA and hence increase in the amount of C9orf72 protein.

Alternatively the agent may bind to a nucleic sequence encoding C9orf72 protein in such a manner that it leads to an increase in the amount of transcribed mRNA encoding the polypeptide. For instance the agent may bind to coding or non-coding regions of the gene or to DNA 5' or 3' of the gene and thereby increase expression of the protein.

In a preferred embodiment of the fifth and sixth aspects of the invention, the agent is C9orf72 protein per se or an active fragment thereof. The protein may be isoform a or b. Preferably the protein is C9orf72 isoform b. In such an embodiment, the C9orf72 protein may be administered directly to the subject in conjunction with a pharmaceutically acceptable carrier.

Alternatively, or additionally, in another embodiment of the fifth and sixth aspects of the invention, treatment may consist of administering a nucleic acid sequence encoding C9orf72 protein or an active fragment thereof to the subject, for example, by gene therapy. Gene therapy consists of the insertion or the introduction of a gene or genes into a subject in need of treatment. In accordance with the present invention, it is preferred that the gene C9orf72 encoding the C9orf72 protein is used. Accordingly, it is preferred that at least one, and preferably, more than one, copy of the C9orf72 gene will be introduced in to a subject to be treated.

It will be appreciated that there is some sequence variability between the sequence of the C9orf72 gene and hence the polypeptide between genuses and species. Hence, it is preferred that the sequence of the gene used in the therapeutic aspects of the invention is from the same genus as that of the subject being treated. For example, if the subject to be treated is mammalian, then the methods according to the invention will use the relevant mammalian gene. It is especially preferred that the gene used is from the same species as that of the subject being treated. For example, if the subject to be treated is human, then the method according to the invention will use the human C9orf72 gene.

Suitably C9orf72 protein for provision as a therapeutic agent may be produced by known techniques. For instance, the protein may be purified from naturally occurring sources of C9orf72 protein. Indeed, such naturally occurring sources of C9orf72 protein may be induced to express increased levels of the protein, which may then be purified using well-known conventional techniques. Alternatively cells that do not naturally express C9orf72 protein may be induced to express such proteins. One suitable technique involves cellular expression of an C9orf72 protein /his construct. The expressed construct may subsequently be highly purified by virtue of the his "tag".

It will be appreciated that C9orf72 protein represents a favourable agent to be administered by techniques involving cellular expression of polynucleotide sequence encoding C9orf72 protein. Such methods of cellular expression are particularly suitable for medical use in which the therapeutic effects of C9orf72 protein are required over a prolonged period of time.

The nucleic acid used in treatments may further comprise elements capable of controlling and/or enhancing C9orf72 expression in the cell being treated. For example, the nucleic acid may be contained within a suitable vector to form a recombinant vector and preferably adapted to produce C9orf72 protein. The vector may for example be a plasmid, cosmid or phage. Such recombinant vectors are highly useful in the delivery systems of the invention for transforming cells with the nucleic acid molecule. Examples of suitable vectors include pCMV6-XL5 (OriGene Technologies Inc), NTC retroviral vectors (Nature Technology Corporation) and adeno-associated viral vectors (Avigen Technology).

For human gene therapy, vectors will be used to introduce genes coding for products with at least 50%, 60%, 70%, 80%, 90%, 95% or 99% identity with the C9orf72 protein sequence provided herein.

When gene therapy is used, it is preferred that at least 2 administrations of 1-1000 million vector units/ml is given at certain intervals, depending on vectors used (the vectors will influence the stability of expression and persistence of C9orf72 in organisms, from only several weeks to permanent expression) and individual requirements of the subject to be treated.

Recombinant vectors may comprise other functional elements to improve the gene therapy. For instance, recombinant vectors can be designed such that they will autonomously replicate in the cell in which they are introduced. In this case, elements that induce nucleic acid replication may be required in the recombinant vector. The recombinant vector may comprise a promoter or regulator to control expression of the gene as required. Alternatively, the recombinant vector may be designed such that the vector and gene integrates into the genome of the cell. In this case nucleic acid sequences, which favour targeted integration (e.g. by homologous recombination) may be desirable. Recombinant vectors may also have DNA coding for genes that may be used as selectable markers in the cloning process.

The C9orf72 gene may (but not necessarily) be one, which becomes incorporated in the DNA of cells of the subject being treated.

The delivery system may provide the nucleic acid encoding C9orf72 or an active fragment or analog thereof to the subject without it being incorporated in a vector. For instance, the nucleic acid molecule may be incorporated within a liposome or virus particle. Alternatively, a "naked" nucleic acid molecule may be inserted into a subject's cells by a suitable means e.g. direct endocytotic uptake. The nucleic acid molecule may be transferred to the cells of a subject to be treated by transfection, infection, microinjection, cell fusion, protoplast fusion or ballistic bombardment. For example, transfer may be by ballistic transfection with coated gold particles, liposomes containing the nucleic acid molecule, viral vectors (e.g. adenovirus) and means of providing direct nucleic acid uptake (e.g. endocytosis) by application of the gene directly.

C9orf72 protein and active fragments thereof; agents as defined herein; and/or nucleic acids may be combined in compositions having a number of different forms depending, in particular on the manner in which the composition is to be used. Thus, for example, the composition may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle of the composition of the invention should be one which is well tolerated by the subject to whom it is given, and preferably enables delivery of the protein, agent or gene to the target cell, tissue, or organ. Hence, it is preferred that C9orf72 protein is delivered by means of a suitably protected carrier particle, for example, a micelle.

Compositions for medical use according to the invention may be used in a number of ways. For instance, systemic administration may be required in which case the compound may be contained within a composition that may, for example, be ingested orally in the form of a tablet, capsule or liquid. Alternatively, the composition may be administered by injection into the blood stream. Injections may be intravenous (bolus or infusion) or subcutaneous (bolus or infusion). The compounds may be administered by inhalation (e.g. intranasally).

Proteins, agents and nucleic acids (as defined herein) may also be incorporated within a slow or delayed release device. Such devices may, for example, be inserted on or under the skin, and the compound may be released over weeks or even months. Such devices may be particularly advantageous when long term treatment according to the invention is required and which would normally require frequent administration (e.g. at least daily injection).

It will be appreciated that the amount of protein, agent and nucleic acid that is required is determined by its biological activity and bioavailability which in turn depends on the mode of administration, physicochemical properties, and whether the medicament is being used as a monotherapy or in a combined therapy. Also, the amount will be determined by the number and state of target cells to be treated. The frequency of administration will also be influenced by the above-mentioned factors and particularly the half-life of the C9orf72 protein and active fragments thereof, agents and nucleic acids within the subject being treated.

Optimal dosages to be administered may be determined by those skilled in the art, and will vary with the particular protein, agent or gene in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations according to the invention and precise therapeutic regimes.

Generally, a daily dose of between 0.01 μg/kg of body weight and 0.5 g/kg of body weight of C9orf72 protein may be used for the prevention and/or treatment of neurodegenerative disease (e.g. FLD or MND). More preferably, the daily dose is between 0.01 mg/kg of body weight and 200 mg/kg of body weight, and most preferably, between approximately 1 mg/kg and 100 mg/kg.

Daily doses may be given as a single administration (e.g. a single daily injection). Alternatively, the protein, agent or gene used may require administration twice or more times during a day. As an example, C9orf72 protein may be administered as two (or more depending upon the severity of the condition) daily doses of between 25 mg and 7000 mg (i.e. assuming a body weight of 70 kg). A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

This invention provides a pharmaceutical composition comprising a therapeutically effective amount of a protein, agent or nucleic acid according to the fifth or sixth aspects of the invention as a drug substance and optionally a pharmaceutically acceptable vehicle. In one embodiment, the amount of drug substance is an amount from about 0.01 mg to about 800 mg. In another embodiment, the amount drug substance is an amount from about 0.01 mg to about 500 mg. In another embodiment, the amount drug substance is an amount from about 0.01 mg to about 250 mg. In another embodiment, the amount of drug substance is an amount from about 0.1 mg to about 60 mg. In another embodiment, the amount of drug substance is an amount from about 0.1 mg to about 20 mg.

A "pharmaceutically acceptable vehicle" as referred to herein is any physiological vehicle known to those of ordinary skill in the art useful in formulating pharmaceutical compositions.

According to a seventh aspect of the present invention, there is provided an agent for preventing or treating mutant C9orf72 mRNA toxicity for use as medicament for the prevention or treatment of neurodegenerative disease.

According to a eighth aspect of the invention there is provided a method of preventing or treating neurodegenerative disease comprising administering to a subject in need of such treatment a therapeutically effective quantity of an agent for preventing or treating mutant C9orf72 mRNA toxicity.

The inventors believe that the expanded 5'-GGCCCC'3' repeat could sequester vital proteins from the cell which ultimately kills it and causes neurodegeneration. Accordingly an antisense agent comprising an oligonucleotide that is the reverse complement to the repeat (i.e. 5'-GGGGCC-3') can be introduced into the cell where it will hybridise to the expanded repeat in mutant mRNA and thereby changing its confirmation and preventing the sequestering of molecules required for cell viability. The agent may comprise one or more copies of the repeat and can be delivered into the cell using gene therapy or other similar nucleic acid delivery methods (e.g. those contemplated above in connection with the fifth or sixth aspects of the invention). Antisense molecules are typically single-stranded nucleic acids, which can specifically bind to a complementary nucleic acid sequence produced by a gene and inactivate it, effectively turning that gene "off". The molecule is termed "antisense" as it is complementary to the gene's mRNA, which is called the "sense" sequence, as appreciated by the skilled person. Antisense molecules are typically are 15 to 35 bases in length of DNA, RNA or a chemical analogue. Antisense nucleic acids were first used experimentally to bind to mRNA and prevent the expression of specific genes. This has lead to the development of "antisense therapies" as drugs for the treatment of medical conditions and antisense drugs have recently been approved by the US FDA for human therapeutic use. Accordingly, by designing an antisense molecule to mutant C9orf72 mRNA it is possible to reduce mRNA toxicity and thereby prevent the development or treat neurodegeneration.

Alternatively, levels of the mRNA transcript containing the mutant and toxic expansion could be reduced by introducing Small interfering RNA molecules (siRNA) specific to the mutant transcript into the appropriate cells in the CNS. Such molecules would reduce the levels of C9orf72 mRNA via RNA interference. siRNA are a class of typically 20-25 nucleotide-long RNA molecules which are involved in the RNA interference pathway (RNAi) and which can specifically interfere with the translation of mRNA. siRNAs have a well defined structure: a short (usually 21-nt) double-strand of RNA (dsRNA) with 2-nt 3' overhangs on either end. Each strand has a 5' phosphate group and a 3' hydroxyl (—OH) group. In vivo this structure is the result of processing by Dicer, an enzyme that converts either long dsRNAs or hairpin RNAs into siRNAs. siRNAs can also be exogenously (artificially) introduced into cells by various transfection methods to bring about the specific knockdown of a gene of interest. Essentially any gene of which the sequence is known can thus be targeted based on sequence complementarity with an appropriately tailored siRNA.

Given the ability to knockdown essentially any gene of interest, RNAi via siRNAs has generated a great deal of interest in both basic and applied biology. There is an increasing number of large-scale RNAi screens that are designed to identify the important genes in various biological pathways. As disease processes also depend on the activity of multiple genes, it is expected that in some situations turning off the activity of a gene with a siRNA could produce a therapeutic benefit. Hence their discovery has led to a surge in interest in harnessing RNAi for biomedical research and drug development. Recent phase I results of therapeutic RNAi trials demonstrate that siRNAs are well tolerated and have suitable pharmacokinetic properties. siRNAs and related RNAi induction methods therefore stand to become an important new class of drugs in the foreseeable future. siRNA molecules designed to mutant C9orf72 mRNA can be used to reduce mRNA toxicity and thereby prevent neurodegeneration. Hence an embodiment of this aspect of the invention is wherein the agent is a siRNA molecule having complementary sequence to mutant C9orf72 mRNA.

A polynucleotide sequence encoding mutant and wild type C9orf72 mRNA are discussed above. Using such information it is straightforward and well within the capability of the skilled person to design siRNA molecules having complementary sequence to mutant C9orf72 mRNA. For example, a simple internet search yields many websites that can be used to design siRNA molecules.

By "siRNA molecule" we include a double stranded 20 to 25 nucleotide-long RNA molecule, as well as each of the two single RNA strands that make up a siRNA molecule.

It is most preferred that the siRNA is used in the form of hair pin RNA (shRNA). Such shRNA may comprise two complementary siRNA molecules that are linked by a spacer sequence (e.g. of about 9 nucleotides). The complementary siRNA molecules may fold such that they bind together.

In preferred embodiments the agent according to the seventh and eight aspects of the invention are administered directly into the Central Nervous System (e.g. by injection).

Screening Methods

A seventh aspect of the invention provides a method of screening for compounds of use in preventing or treating neurodegenerative diseases wherein a non-human animal is administered a test compound and the effect of the test compound on the amount and/or function of C9orf72 protein is assessed and wherein an increase in the amount and/or function of C9orf72 protein indicates the tested compound is a candidate drug-like compound or lead compound for preventing or treating neurodegenerative disease.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry or by techniques of molecular biology or biochemistry. Such compounds are preferably small molecules, which may be of less than 5000 daltons and which may be water-soluble although candidate biologics may also be screened. A drug-like compound may additionally exhibit features of selective interaction with a particular protein or proteins and be bioavailable and/or able to penetrate target cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

The methods of the seventh aspect of the invention include a step of assessing the effect of a test compound on the amount and/or function of C9orf72 protein.

In common with all these methods is the need for a "reference sample", i.e. a sample of protein or nucleic acid taken from an animal or cell which has not been exposed to the test compound. By comparing the amount and/or function of C9orf72 protein in a sample of protein or nucleic acid taken from an animal or cell which has not been exposed to the test compound, to the amount and/or function of C9orf72 protein in a sample of protein or nucleic acid taken from an animal or cell which has been exposed to the test compound it is possible to determine the effect of the test compound on the amount and/or function of C9orf72 protein. This will show the test compound(s) to produce an elevation, reduction or no effect on expressed levels of the C9orf72 protein, or a potentiation, inhibition or no effect on the function of C9orf72 protein.

The step of assessing the amount and/or function of C9orf72 protein may be performed using a number of different methods. For example, a method of assessing the effect of the test compound on the amount of C9orf72 protein is to quantify the amount of said protein. Alternatively, the effect of the test compound can be determined by quantifying the amount of nucleic acid, preferably mRNA, encoding the C9orf72 protein.

A further method of assessing the effect of the test compound is to assess the effect of the test compound on the function of C9orf72.

The screening methods of the invention can be used in "library screening" methods, a term well known to those skilled in the art.

The invention will be further described, by way of Example, and with reference to the following figures:—

FIG. 1. Pedigrees of patients carrying the C9ORF72 GGGGCC hexanucleotide repeat expansion. (A-E) Pedigrees of patients with the hexanucleotide repeat expansion. Mutant alleles are shown by mt, whereas wild-type alleles are indicated by wt. Inferred genotypes are in brackets. Probands are indicated by arrows. Sex of the pedigree members is obscured to protect privacy.

FIG. 2. Frequency distribution of GGGGCC hexanucleotide repeat lengths in ALS cases and control samples based on the repeat-primed PCR assay. (A) Histogram of repeat length observed in Finnish cases (n=402); (B) Histogram of repeat length observed in Finnish controls (n=478); (C) Histogram of repeat length in familial ALS cases of general European (non-Finnish) descent (n=260); (D) Histogram of repeat length in control samples of European descent (n=389) and Human Gene Diversity Panel samples (n=300). A bimodal distribution is evident with samples carrying the repeat expansion showing 30 or more repeats (using the repeat-primed PCR assay) and control samples having less than 20 repeats.

Figure 3A:
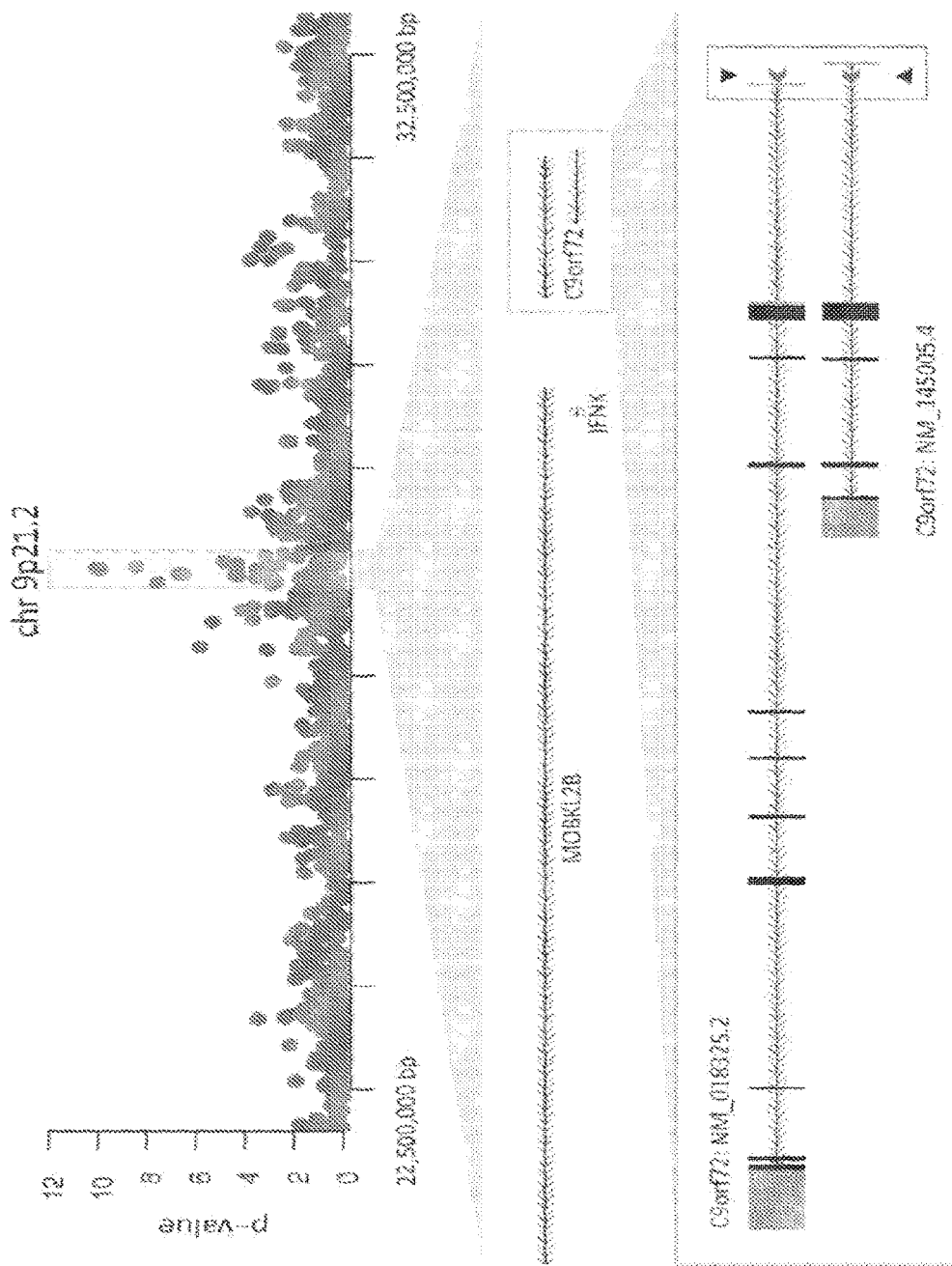
Figure 3B:
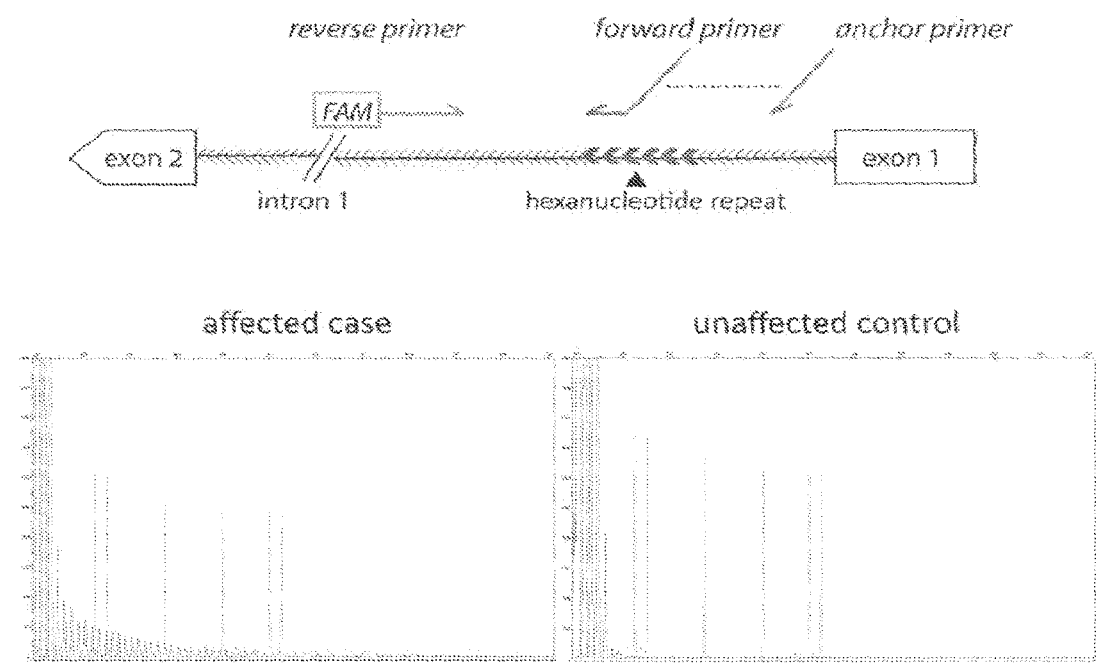

FIG. 3. GGGGCC hexanucleotide repeat expansion in the first intron and promoter of C9ORF72. (A) Physical map of the chromosome 9p21 ALS/FTD locus showing the p-values for SNPs genotyped in the previous GWAs (Laaksovirta et al., 2010), the location of the GWAs association signal within a 232 kb block of linkage disequilibrium, the MOBKL2B, IFNK and C9ORF72 genes within this region, and the position of the GGGGCC hexanucleotide repeat expansion within the two main transcripts of C9ORF72; (B) A graphical representation of primer binding for repeat-primed PCR analysis is shown in the upper panel. In the lower panel, capillary-based sequence traces of the repeat-primed PCR are shown. Orange lines indicate the size markers, and the vertical axis represents fluorescence intensity. A typical saw tooth tail pattern that extends beyond the 300 bp marker with a 6 bp periodicity is observed in the case carrying the GGGGCC repeat expansion; (C) Detection of the repeat expansion in the lymphoblastoid cell line from the affected proband ND06769 by FISH using Alexa Fluor 488-labeled oligonucleotide probe seen as a green fluorescence signal on one of the homologues of chromosome 9p (i) consistent with a repeat expansion size of more than 1.5 kb. DAPI-inverted image (ii & iv). No hybridization signal was detected on metaphase cells or interphase nuclei from the lymphoblastoid cell line of control individual ND 11463 (iii) and 5 other normal control individuals (data not shown). Cells were counterstained with 4',6-diamidino-2-phenylindole (DAPI, red color), ×60 objective.

Figure 4:
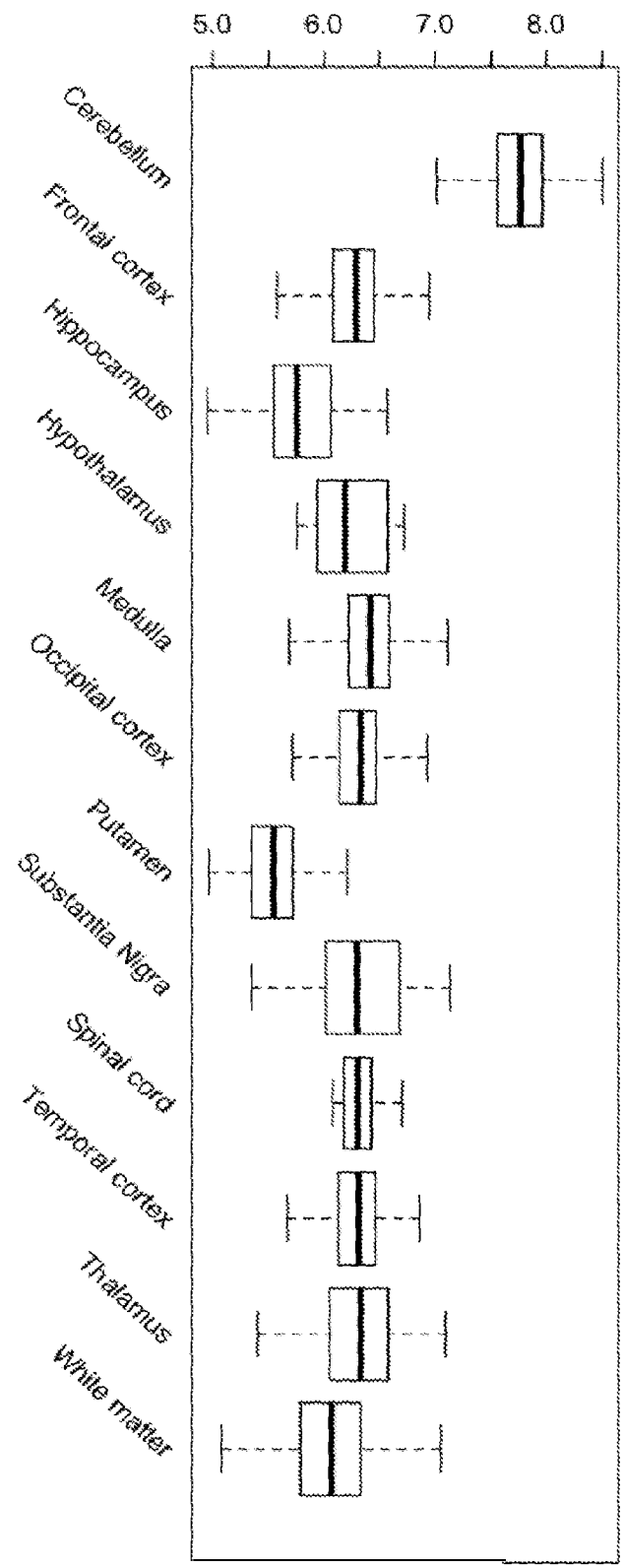
Figure 4:
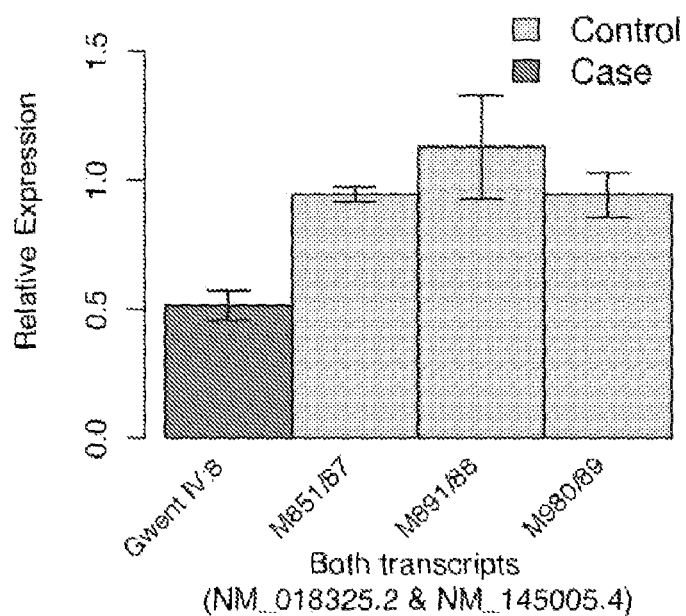
Figure 4:
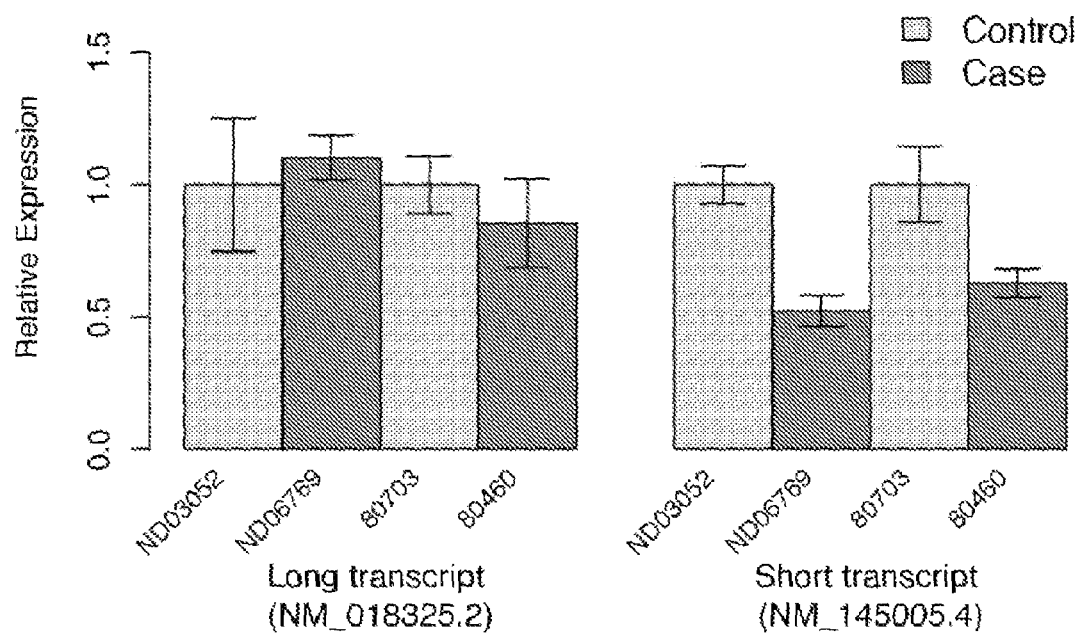

FIG. 4. Expression analysis of C9ORF72 RNA. (A) Expression array analysis of C9ORF72 in various human CNS regions obtained from neuropathologically normal individuals (n=137); (B) mRNA expression in frontal cortex from an affected member of the GWENT#1 kindred and neurologically normal controls (n=3). Measurement was by RT-PCR using primers to detect all C9ORF72 transcripts. The data indicate the mean±SD relative to the levels of GAPDH; (C) mRNA expression in lymphoblastoid cell lines from cases (n=2) and neurologically normal controls (n=2). Measurement was by RTPCR using primers that detect only the NM_018325.2 (left panel) and NM_145005.4 (right panel) transcripts of C9ORF72. The data indicate the mean±SD relative to the levels of GAPDH.

Figure 5:
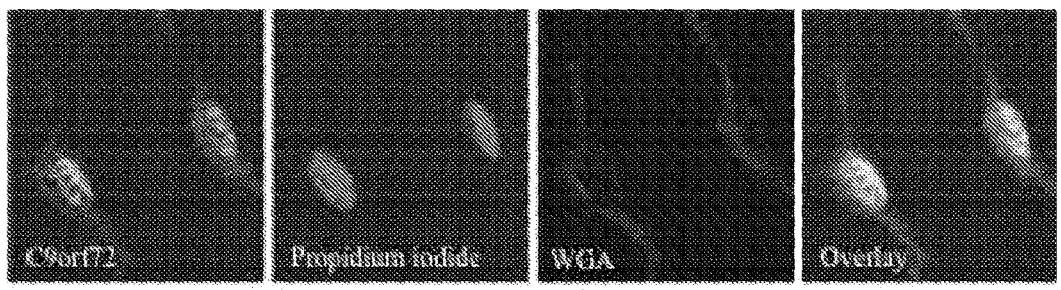
Figure 5:
Figure 5:
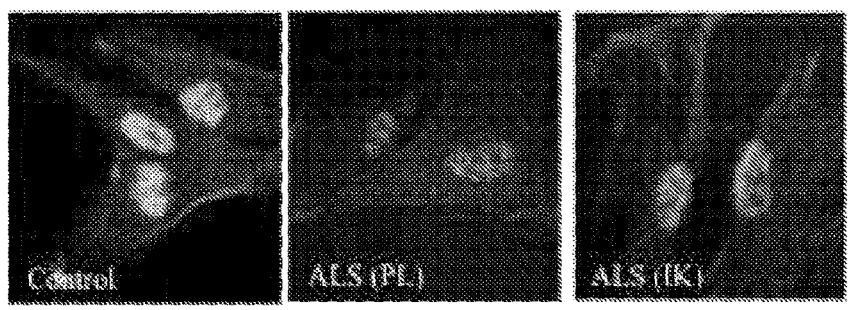
Figure 5:
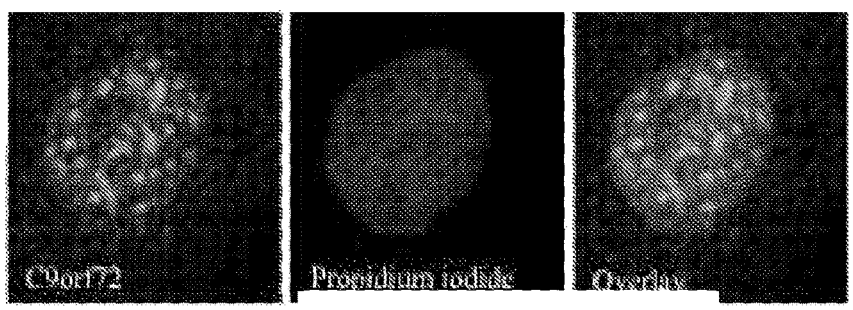
Figure 5:
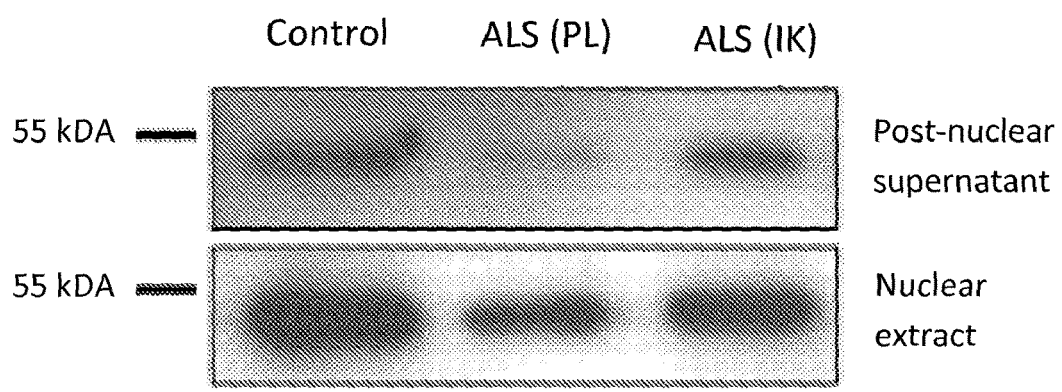
Figure 5:
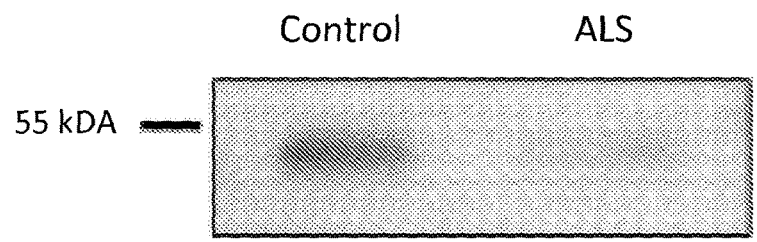

FIG. 5. Analysis of C9ORF72 protein levels in cell lines from ALS patients. (A) Immunocytochemical analysis of C9ORF72 in mouse motor neuron cell line (NSC-34). Green signals represent C9ORF72. Anti-C9ORF72 antibody staining is predominantly localized within the nucleus with mild cytosolic localization in addition; (B) Immunocytochemistry for C9ORF72 in human-derived primary fibroblasts from cases (n=2) and a control cell line (n=1). Green signals represent C9ORF72. Both ALS cell lines show reduced protein level overall and their cytosol/nuclear ratio is increased as compared to the control cell line; (C & D) Immunoblotting of C9ORF72 (55 kDa) confirmed the lower level of C9ORF72 protein in lymphoblastoid cell lines from ALS cases relative to control cell lines in total, and in both the nucleus and the cytosolic cellular compartments.

Figure 6:
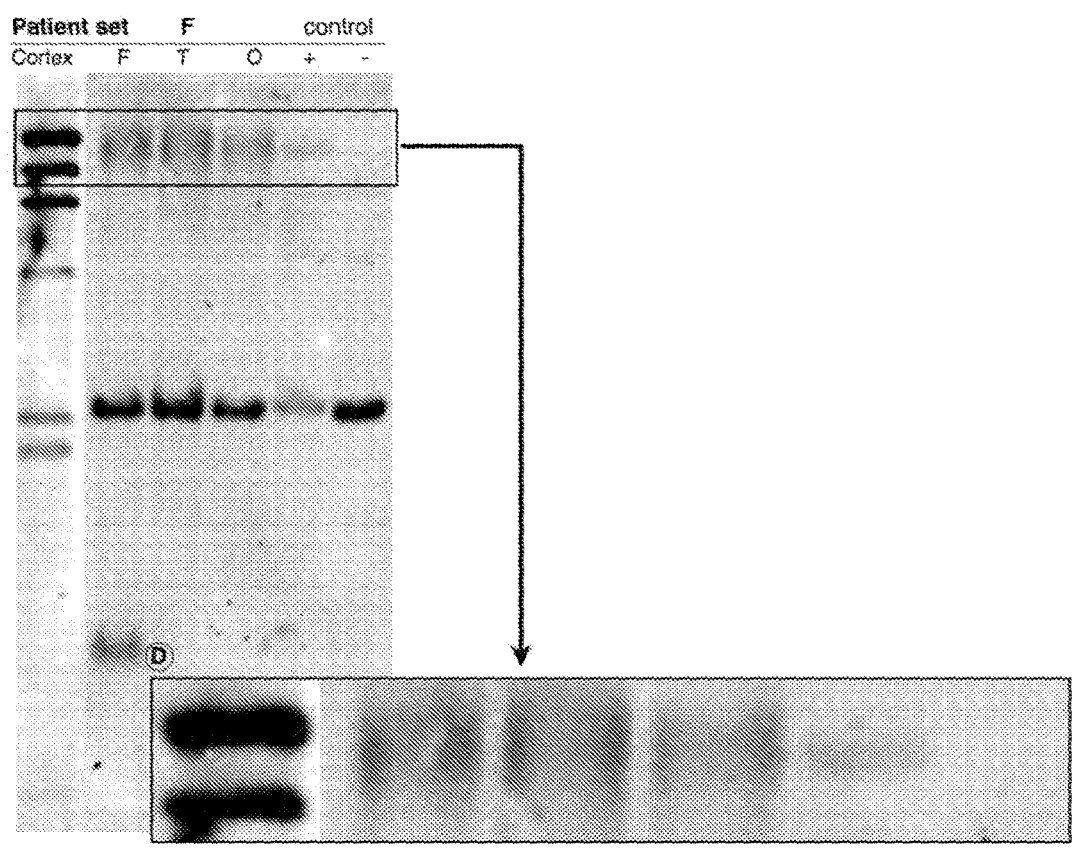

FIG. 6. A Southern Blot analysis illustrating the GGGGCC repeat expansion in samples from an MND/ALS patient. The figure shows an expansion of approximately 1100 repeats (approximately 9 kb) in tissue from different brain regions of an ALS subject (F=frontal; T=temporal; and O=Occipital) and a cell line controls (+ and −ve for the repeat).

Figure 7:
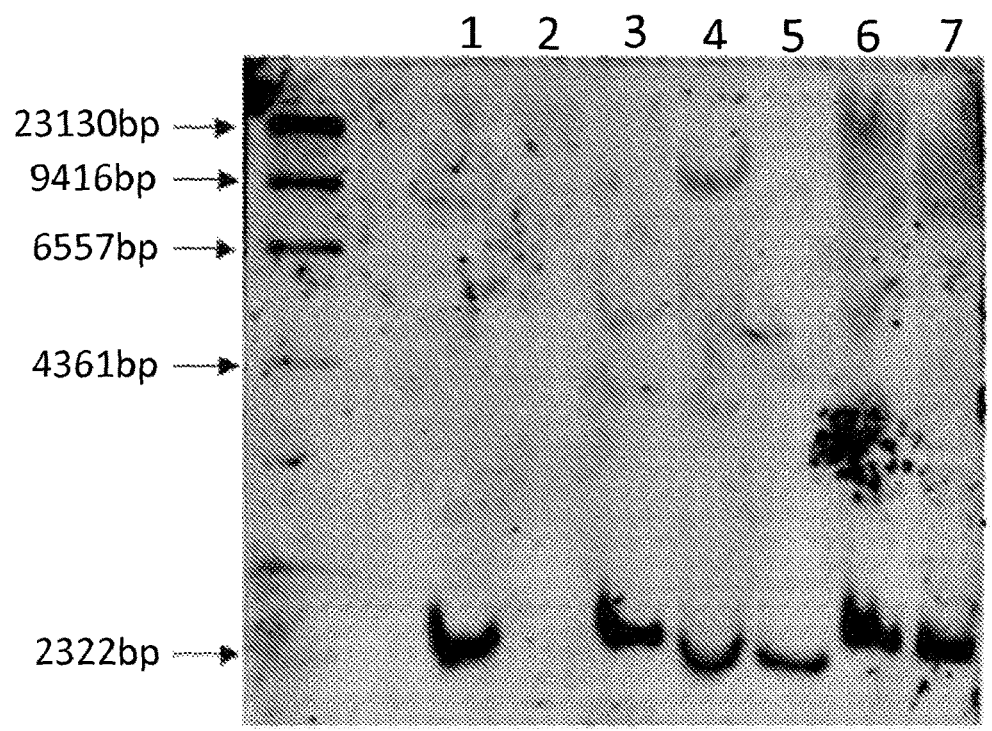

FIG. 7. A further Southern Blot analysis illustrating the GGGGCC repeat expansion in samples from subjects with FTD or ALS/MND. The figure shows that expansion of the repeat was present in a subject with MND/ALS (lane 1); a subject with FTD/MND (lane 3): a subject (age of onset 52) with FTD (lane 6); and a subject (age of onset 56) with FTD (lane 7) as discussed in Example 2.

EXAMPLE 1

The chromosome 9p21 motor neuron disease/amyotrophic lateral sclerosis-frontotemporal dementia (MND/

ALS-FTD) locus contains one of the last major unidentified autosomal dominant genes underlying a common neurodegenerative disease. The inventors have established that a founder haplotype is present in the majority of cases linked to this region, and that this risk haplotype accounts for more than one third of familial MND/ALS cases in the Finnish population. The haplotype covers three known genes, MOBKL2b, IFNK and C9orf72.

The inventors have now established that there is a GGC-CCC hexanucleotide repeat expansion in the first intron of C9orf72 on the affected haplotype. This repeat segregates perfectly with disease in the Finnish population, underlying 46.0% of familial MND/ALS and 21.1% of sporadic ALS in that population. Taken together with the D90A SOD1 mutation, 87% of familial ALS in Finland is now explained by a simple monogenic cause. The repeat expansion also segregates with disease in several large families linked to the region, and is present in one third of familial ALS cases of outbred European descent making it the most common genetic cause of this fatal neurodegenerative disease identified to date 1.1 Introduction Amyotrophic lateral sclerosis (ALS, OMIM #105400) is a fatal neurodegenerative disease characterized clinically by progressive paralysis leading to death from respiratory failure, typically within two to three years of symptom onset. ALS is also known as Motor Neuron Disease (MND) as referred to herein. ALS is the third most common neurodegenerative disease in the Western World and there are currently no effective therapies. Approximately 5% of cases are familial in nature, whereas the bulk of patients diagnosed with the disease are classified as sporadic as they appear to occur randomly throughout the population. There is growing recognition, based on clinical, genetic, and epidemiological data, that ALS and frontotemporal dementia (FTD, OMIM #600274) represent an overlapping continuum of disease, characterized pathologically by the presence of TDP-43 positive inclusions throughout the central nervous system.

To date, a number of genes have been discovered as causative for classical familial ALS, namely SOD1, TARDBP, FUS, OPTN and VCP. These genes cumulatively account for 25% of familial cases, indicating that other causative genes remain to be identified. Each new gene implicated in the etiology of ALS or FTD provides fundamental insights into the cellular mechanisms underlying neuron degeneration, as well as facilitating disease modeling and the design and testing of targeted therapeutics; Thus, the identification of new ALS and FTD genes is of great significance.

Linkage analysis of kindreds involving multiple cases of ALS, FTD and ALS-FTD had suggested that there was an important locus for the disease on the short arm of chromosome 9. Using a genome-wide association (GWAs) approach, the inventors have established that this locus on chromosome 9p21 accounted for nearly half of familial ALS and nearly one quarter of all ALS cases in a cohort of 405 Finnish patients and 497 control samples (Laaksovirta et al. (2010) Lancet Neurology 9, 978-985). A meta-analysis involving 4,312 cases and 8,425 controls confirmed that chromosome 9p21 was a major signal for ALS (Shatunov et al. (2010) Lancet Neurology 9, 986-994). A recent GWAs for FTD also identified this locus (Van Deerlin et al. (2010) Nature Genetics 42 234-239). Analysis in the Finnish population narrowed the association to a 232 kb block of linkage disequilibrium, and allowed the identification of a founder haplotype that increased risk of disease by over twenty-fold. The associated haplotype appears to be the same in all European-ancestry populations, and several families previously shown to have genetic linkage to the chromosome 9p21 region also share this risk haplotype.

The inventors have previously identified an ALS-FTD family from the UK and an apparently unrelated ALS-FTD family from the Netherlands that showed positive linkage to the chromosome 9p21 region. Using these families and the Finnish ALS cases that had previously been used to identify the chromosome 9p21 association signal, we undertook a methodical assessment of the region using next-generation sequencing technology in an attempt to identify the genetic lesion responsible for disease.

1.2 Methods 1.2.1 Patients and Material

The inventors studied a four-generation Welsh family (GWENT#1) in which 9 individuals had been diagnosed with ALS and/or FTD, and were known to share the chromosome 9p21 risk haplotype. The pedigree of this family is shown in FIG. 1A, and the clinical features have been previously reported (Pearson et al., (2011) Journal of Neurology 258 p647-655). DNA samples were available from four individuals of generations IV who had been diagnosed with ALS and/or FTD. Flowsorting of chromosome 9 was performed on lymphoblastoid cell lines from an affected case ND06769 (IV-3, FIG. 1A) and a neurologically normal population control ND11463 at Chrombios GmbH (www.chrombios.com).

The inventors also analyzed an apparently unrelated six-generation Dutch ALS/FTD family (DUTCH#1, FIG. 1B), in which linkage and haplotype analysis showed significant linkage to a 61 Mb region on chromosome 9p21 spanning from rs10732345 to rs7035160 and containing 524 genes and predicted transcripts. Genomic regions from all exons and exon-intron boundaries, 5' UTRs, 3' UTRs, ~650 bp of upstream promoter regions, sno/miRNA loci, and conserved regions were captured using SureSelect target enrichment technology (Agilent Inc., Santa Clara Calif., USA). In total, 43,142 unique baits were used for these experiments covering a total of 2.58 MB in the chromosome 9p FTD/ALS locus (c9FTD/ALS).

For subsequent mutational screening of the GGGGCC hexanucleotide repeat expansion, we used DNA from 402 Finnish ALS cases and 478 Finnish neurologically normal individuals that had previously been used to identify the chromosome 9p21 association signal (Laaksovirta et al., (2010) Lancet Neurology 9 p978-985). An additional 260 DNA samples were obtained from affected probands in unrelated ALS families (198 US cases, 36 German cases, and 26 Italian cases), and from 75 Finnish individuals who had presented with isolated FTD. Control samples consisted of 242 neurologically normal US individuals obtained from the NINDS repository at Coriell, 64 neurologically normal German individuals, and 83 neurologically normal Italian individuals. An additional series of 300 anonymous African and Asian samples that are part of the Human Gene Diversity Panel were included in the mutational analysis as controls to evaluate the genetic variability of the repeat expansion in non-Caucasian populations. Demographics and clinical features of these samples are summarized in Table 1 and in Laaksovirta et al, 2010 (supra). Appropriate institutional review boards approved the study.

TABLE 1

Demographic and clinical details of European-descent familial ALS, Finnish FTD patients and neurologically normal controls.

| | European-descent Familial ALS Case (n = 260)* | European-descent Controls (n = 389) | Finnish FTD Case (n = 75) |
|---|---|---|---|
| Mean age (range) | 56.9 (15-87) | 45.1 (4-101) | 58.4 (38-79) |
| Male (%) | 139 (53.7%) | 183 (47.0%) | 34 (45.3) |
| Female (%) | 120 (46.3) | 206 (53.0%) | 41 (54.7%) |
| Familial (%) | 260 (100%) | — | 27 (36.0%) |
| Sporadic (%) | 0 (0%) | — | 48 (64.0%) |
| Site of symptom onset: | | | |
| Bulbar-onset (%) | 49 (26.2%) | — | — |
| Spinal-onset (%) | 138 (73.8%) | — | — |
| Behaviour variant FTD (%) | — | — | 48 (64.0%) |
| Progressive non-fluent aphasia (%) | — | — | 20 (26.7%) |
| Semantic dementia (%) | — | — | 7 (9.3%) |

*Data missing for age at onset (n = 4), gender (n = 1) and site of onset (n = 73)

1.2.2 Next Generation Sequencing

Paired-end sequencing was performed on a next-generation HiSeq2000 sequencer according to the manufacturer's protocol (Illumina Inc., San Diego, Calif., USA). This generated 56.7 gigabases of alignable sequence data for the control sample ND11463 (mean read depth for the chromosome 9 region 27,367,278 to 27,599,746 bp=42.2) and 114.4 gigabases for the case sample ND06769 (mean read depth=170.4). Sequence alignment and variant calling were performed against the reference human genome (UCSC hg 18). Sequencing reads were aligned using BWA (Li and Durbin, 2009). Sorting, indexing, read duplicate removal and merging of BAM files was preformed with Picard (http://picard.sourceforge.net). The Genome Analysis Toolkit was used to perform base quality score recalibration and to call variants (McKenna et al., 2010). SNPs identified within CEU individuals from the 1000 Genomes project (April 2009 release, www.1000genomes.org) or in dbSNP (http://www.ncbi.nlm.nih.gov/projects/SNP/, Build 132) were excluded. The remaining variants were annotated to RefSeq transcripts and protein coding variants prioritized for examination.

1.2.3 Repeat-Primed PCR

Repeat-primed PCR was performed as follows: 100 ng of genomic DNA were used as template in a final volume of 28 ul containing 14 ul of FastStart PCR Master Mix (Roche Applied Science, Indianapolis, Ind., USA), and a final concentration of 0.18 mM 7-deazadGTP (New England Biolabs Inc., Ipswich, Mass., USA), Ix Q-Solution (Qiagen Inc., Valencia, Calif., USA), 7% DMSO (Qiagen), 0.9 mM MgCl$_2$ (Qiagen), 0.7 uM reverse primer consisting of ~four GGGGCC repeats with an anchor tail, 1.4 uM 6FAMfluorescent labeled forward primer located 280 bp telomeric to the repeat sequence, and 1.4 uM anchor primer corresponding to the anchor tail of the reverse primer (sequences listed in 1.2.8). (A touchdown PCR cycling program was used where the annealing temperature was gradually lowered from 70° C. to 56° C. in 2° C. increments with a 3-minute extension time for each cycle.

Figure 2A:
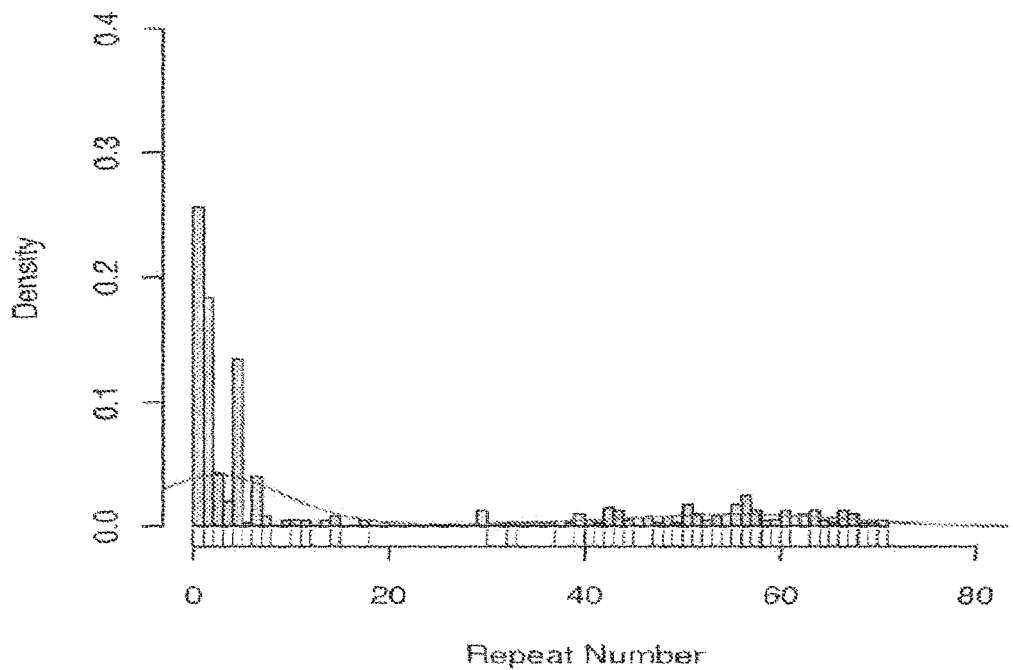
Figure 2B:
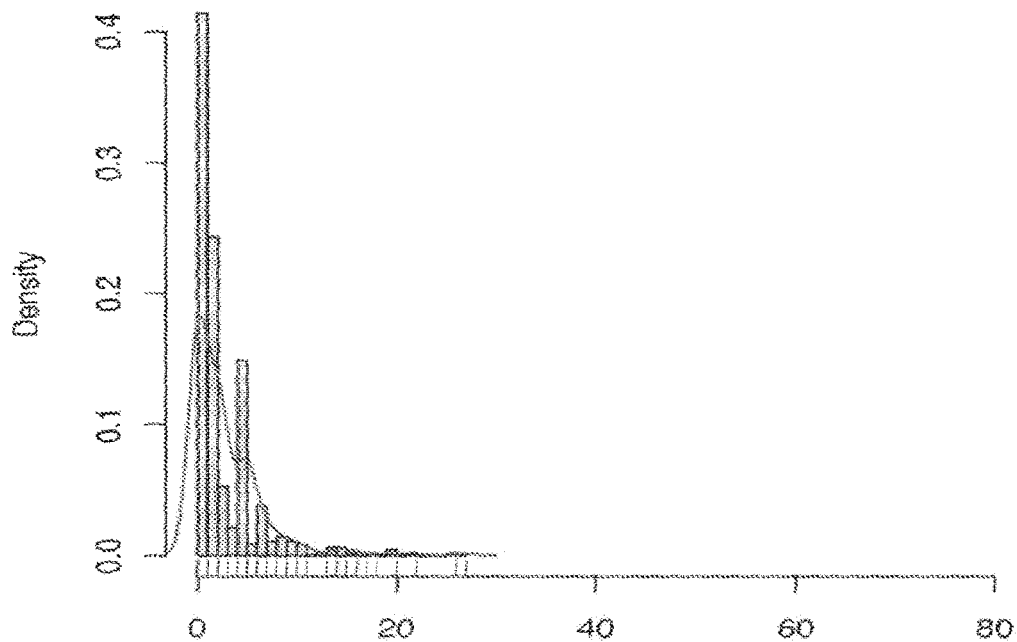

The repeat-primed PCR is designed so that the reverse primer binds at different points within the repeat expansion to produce multiple amplicons of incrementally larger size. The lower concentration of this primer in the reaction means that it is exhausted during the initial PCR cycles, after which the anchor primer is preferentially used as the reverse primer. Fragment length analysis was performed on an ABI 3730x1 genetic analyzer (Applied Biosystems Inc., Foster City, Calif., USA), and data analyzed using GeneScan software (version 4, ABI). Repeat expansions produce a characteristic sawtooth pattern with a 6-bp periodicity (FIG. 2B).

1.2.4 Statistical Analysis

Association testing was performed using the fisher exact test within the PLINK software (version 1.7).

1.2.5 FISH Analysis

Metaphase and interphase FISH analysis of lymphoblastoid cell lines ND06769 (case IV-3 from GWENT#1, FIG. 1A), ND08554 (case II-2 from NINDS0760, FIG. 1E), ND11463 (control), ND11417 (control), ND08559 (unaffected spouse II-3 from NINDS0760), ND03052 (unaffected relative IV-1 from GWENT#1) and ND03053 (unaffected relative III-9 from GWENT#1), as well as a fibroblast cell line (Finnish sample ALS50)) was performed using Alexa fluor 488-labeled GGCCCCGGCCCCGGCCCCGGCC oligonucleotide probe (SEQ ID No. 7) (Eurofins MWG operon, Hunstville, Ala., USA) designed against the repeat expansion. The hybridization was performed in low stringency conditions with 50% Formamide/2×SSC/10% Dextran Sulphate co-denaturation of the slide/probe, 1-hour hybridization at 37° C., followed by a 2-minute wash in 0.4×SSC/0.3% Tween 20 at room temperature. Slides were counterstained with DAPI. FISH signals were scored with a Zeiss epifluorescence microscope Zeiss Axio Imager-2 (Carl Zeiss Microimaging Thornwood, N.Y., USA) equipped with a DAPI/FITC/Rhodamine single band pass filters (Semrock, Rochester, N.Y.) using 40-60× objectives.

1.2.6 RNA Expression

Expression profiling on Affymetrix GeneChip Human Exon 1.0 ST Arrays (Affymetrix, UK) was performed on CNS tissue obtained from 137 neurologically normal individuals at AROS Applied Biotechnology AS company laboratories (www.arosab.com/) (Trabzuni et al., 2011). Gene-level expression was calculated for C9ORF72 based on the median signal of probe 3202421. Date of array hybridization and brain bank were included as co-factors to eliminate batch effects.

For RT-PCR, RNA was extracted from cell pellets using Trizol (Invitrogen, Paisley, UK), and first strand cDNA synthesized using random primers using the Superscript II cDNA Synthesis Kit (Invitrogen). Real-time PCR analyses for the short and long variants of C9ORF72 and GAPDH were performed using the ABI 7900 Sequence Detection System instrument and software (Applied Biosystems). Samples were amplified in quadruplicate in 10 ul volumes using the Power SYBR-green master mix (Applied Biosystems), and 10 pM of each forward and reverse primer (see 1.2.8 for primer sequences), using Applied Biosystems standard cycling conditions for real time PCR (initial denaturation at 95° C. for 10 minutes, followed by 40 cycles of 95° C. for 15 seconds, 60° C. for 1 minute).

1.2.7 Immunocytochemistry and Immunoblotting

Cells were fixed with ice-cold methanol for 2 min and blocked with 10% FBS for 30 min at 37° C. Primary antibody (anti-C9ORF72 antibody by Santa Cruz, 1:30) and secondary antibody (Alexa488-conjugated anti-rabbit antibody by Invitrogen, 1:200) were diluted in Renton et al 5%

FBS and incubated at 37° C. for 3 hours or 30 minutes, respectively. The cells were then treated with 5 µg/ml of Alexa633-conjugated wheat germ agglutinin (Invitrogen) in PBS for 10 min at room temperature (to detect cellular membranes), followed by incubation with 2 µg/ml propidium iodide (Invitrogen) in PBS for 3 minutes (to stain the nuclei). The cells were imaged with a TCS SP2 confocal microscope (Leica). The biochemical cell fractionation was performed as described (DeBose-Boyd et al., (1999) Cell 99 p703-712). Protein determinations were done by using Bio-Rad protein assay, and immunoblotting with anti-C9ORF72 antibody (Santa Cruz, 1:300 dilution) was performed as described (Holtta-Vuori et al., (2002) Molecular Biology of the Cell 13 p3107-3122).

1.2.8 Primers Used for Repeat-Primed PCR, FISH and RT-PCR

For Repeat-Primed PCR:

| Primer name | Primer sequence |
|---|---|
| Forward primer | 6-FAM-AGTCGCTAGAGGCGAAAGC (SEQ ID No. 4) |
| Reverse primer | TACGCATCCCAGTTTGAGACGGGGCCGGGGCC GGGGCCGGGG (SEQ ID No. 5) |
| Anchor primer | TACGCATCCCAGTTTGAGACG (SEQ ID No. 6) |

These repeat-primed PCR primers represent preferred primers for use in PCR based embodiments of the first aspect of the invention. Conventional PCR techniques may be applied to genomic DNA samples utilising such primer. A skilled person will appreciate that alternative primer set can be designed given knowledge of the location of the PCR target region (i.e. the C9orf72 gene mutation).

For FISH Analysis:

| Primer name | Primer sequence |
|---|---|
| Probe | alexa fluor 488-GGCCCCGGCCCCGGCCCCGGCC (SEQ ID No. 7) |

For Quantification of Human C9ORF72 Transcript NM_018325.2:

| Primer name | Primer sequence |
|---|---|
| C9ORF72 Forward | GAAATCACACAGTGTTCCTGAAGAA (SEQ ID No. 8) |
| C9ORF72 Reverse | AGCTGATGGCATTGAGAAGAAAG (SEQ ID No. 9) |
| GAPDH Forward | CCTGTTCGACAGTCAGCCG (SEQ ID No. 10) |
| GAPDH Reverse | CGACCAAATCCGTTGACTCC (SEQ ID No. 11) |

For Quantification of Human C9ORF72 Transcript NM_145005.4:

| Primer name | Primer sequence |
|---|---|
| C9ORF72 Forward | GAAATCACACAGTGTTCCTGAAGAA (SEQ ID No. 8) |
| C9ORF72 Reverse | ATCTGCTTCATCCAGCTTTTATGA (SEQ ID No. 12) |
| GAPDH Forward | CCTGTTCGACAGTCAGCCG (SEQ ID No. 10) |
| GAPDH Reverse | CGACCAAATCCGTTGACTCC (SEQ ID No. 11) |

1.3 Results

Figure 1B:
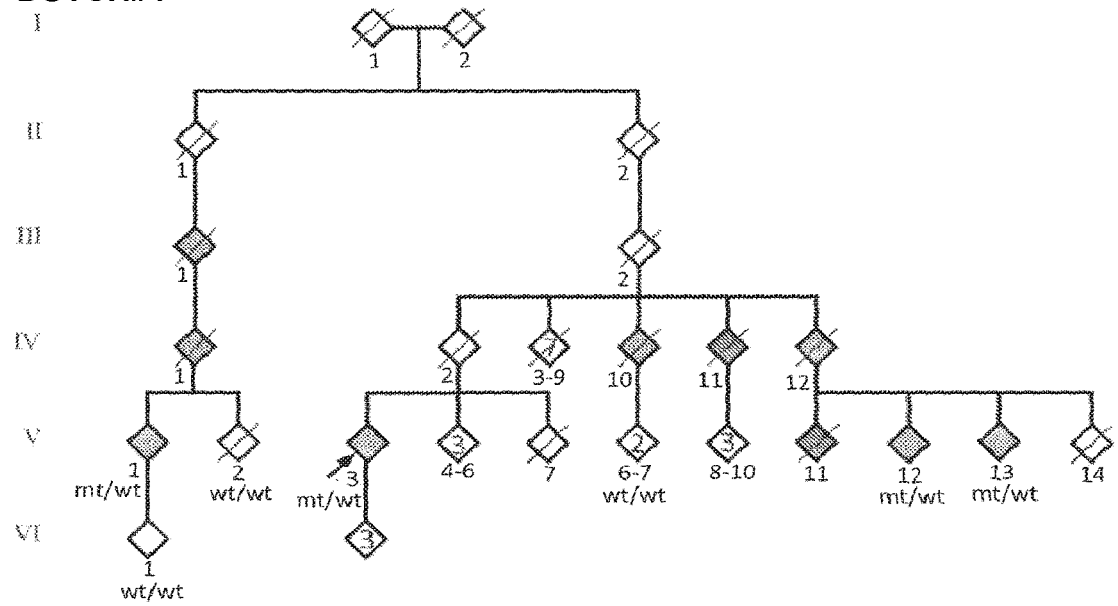

We undertook massively parallel, next-generation, deep re-sequencing of the chromosome 9p21 region in (a) DNA that had been flow-sorted enriched for chromosome 9 obtained from an affected member of the GWENT#1 kindred (IV-3, FIG. 1A; Coriell ID ND06769) and from a neurologically normal control (ND11463); and (b) DNA that had been enriched for the target region using custom oligonucleotide baits obtained from 3 cases and 5 unaffected members of the DUTCH#1 kindred (V-1, V-3 & V-12, and V-2, V4, V5, VI-1 & spouse of V-1; FIG. 1B).

This analysis identified a hexanucleotide repeat expansion GGGGCC located 63 base pairs (bp) centromeric to the first exon of transcript NM_018325.2 of C9ORF72 in the affected cases that was not present in the control samples. The repeat expansion also lies within the first intron of the other major transcript of C9ORF72 (RefSeq accession number NM_145005.4, FIG. 2A).

We next used a repeat-primed PCR method to screen case and control samples for the presence of the GGGGCC hexanucleotide repeat expansion (see FIG. 2B and Experimental Procedures for detailed explanation) (Kobayashi et al., (2011) American Journal of Human Genetics 89 p121-130; Warner et al., (1996) Journal of Medical Genetics 33 p1022-1026). The nature of the repeat-primed PCR assay means that it can detect a maximum of ~60 repeats, and thus the repeat length in a sample carrying the expansion could be far greater than the estimation provided by this technique. Despite this, the assay is an accurate and rapid system that allows samples to be categorized into those that carry a pathogenic repeat expansion (greater than 30 repeats) and those that carry only wild-type alleles (less than 20 repeats). The frequency distribution of the GGGGCC hexanucleotide repeat expansion lengths in ALS cases and control samples based on the repeat-primed PCR assay is shown in FIG. 3.

Using the repeat-primed PCR method, we confirmed that the expanded hexanucleotide repeat was present in the affected members of the GWENT#1 and DUTCH#1 kindreds (IV-3, IV-5, IV-7 & IV-8 in GWENT#1 and V-1, V-3, V-14 & V-15 in DUTCH#1, FIGS. 1A and 1B), and that the expansion was absent from asymptomatic family members (III-1, 111-7 & IV-1 in GWENT#1 and V-2, V-8, V-9 & VI-1 in DUTCH#1).

In the Finnish cohort of 402 ALS cases and 478 controls, repeat-primed PCR analysis showed the hexanucleotide repeat to be expanded in 113 (28.1%) cases and 2 of the controls (fisher test p-value for allelic association=$8.1 \times 10^{-38}$; OR=78.0, 95% CI=19.2-316.8). Overall, 52 (46.0%) of the Finnish familial ALS cases had the expansion (p-value=$3.7 \times 10^{-37}$; OR=140.9, 95% CI=34.0-583.9), and 61 (21.1%) of the sporadic cases had the expansion (p-value=$1.7 \times 10^{-24}$; OR=56.1, 95% CI 13.6-230.2). The average number of repeats detected by the PCR assay in the Finnish cases carrying the expansion was 53 (range, 30 to 71)) compared to an average of 2 (range, 0 to 22) repeats observed in the 476 controls that did not carry the expansion, thereby allowing for robust classification of samples (see FIGS. 3A & 3B).

Of the 113 familial and sporadic cases that carried the hexanucleotide repeat expansion, two-thirds (n=76, 67.3%)

carried the previously identified chromosome 9p21 founder risk haplotype haplotype (Laaksovirta et al., (2010) supra). In contrast, only one of the Finnish controls samples that carried the expansion also carried the risk haplotype.

Figure 1E:
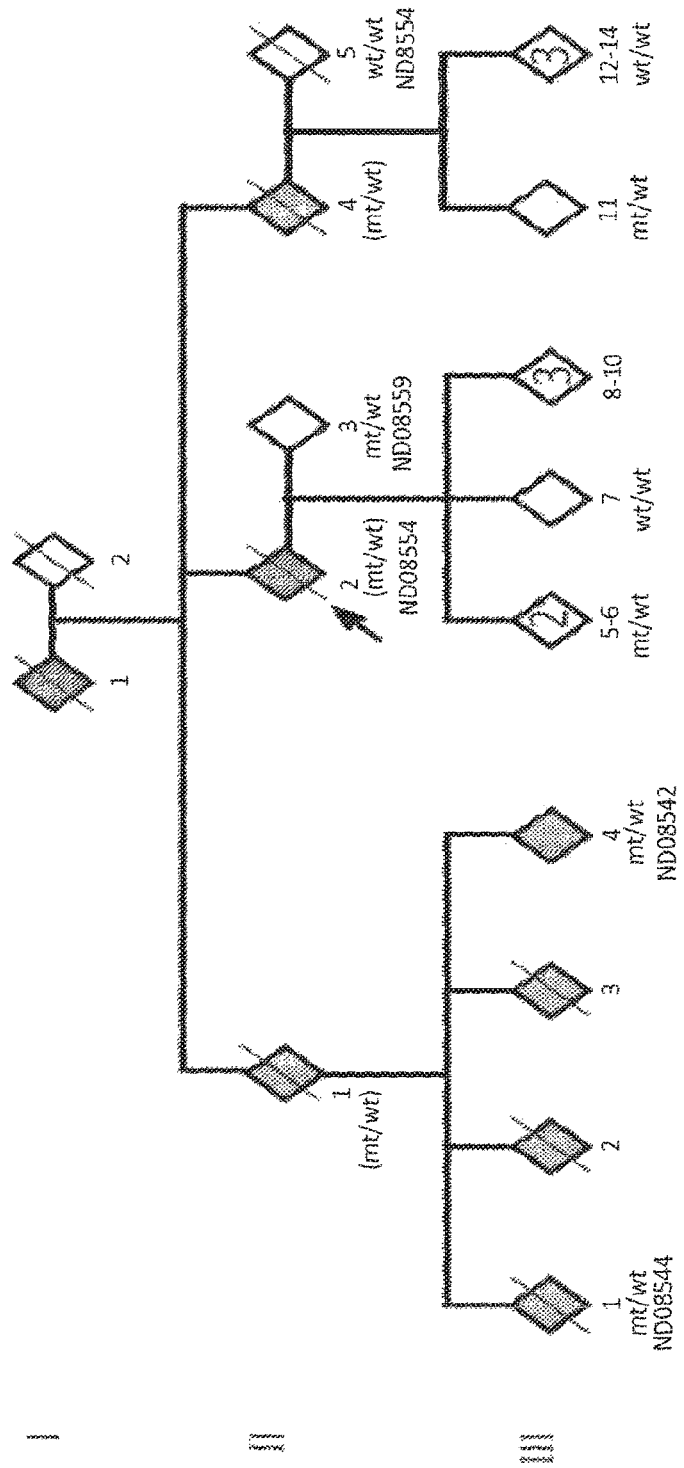
Figure 2C:
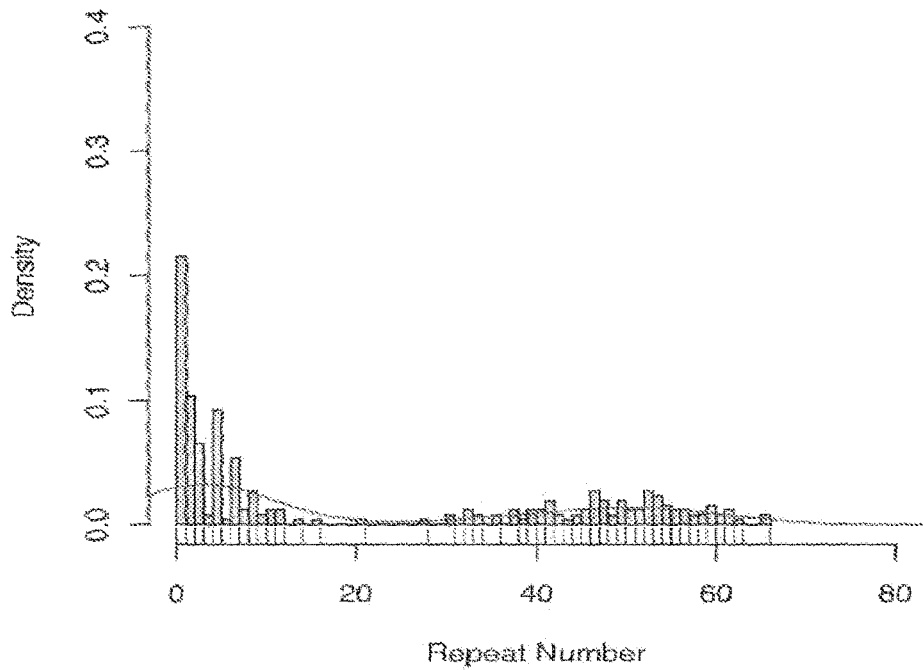
Figure 2D:
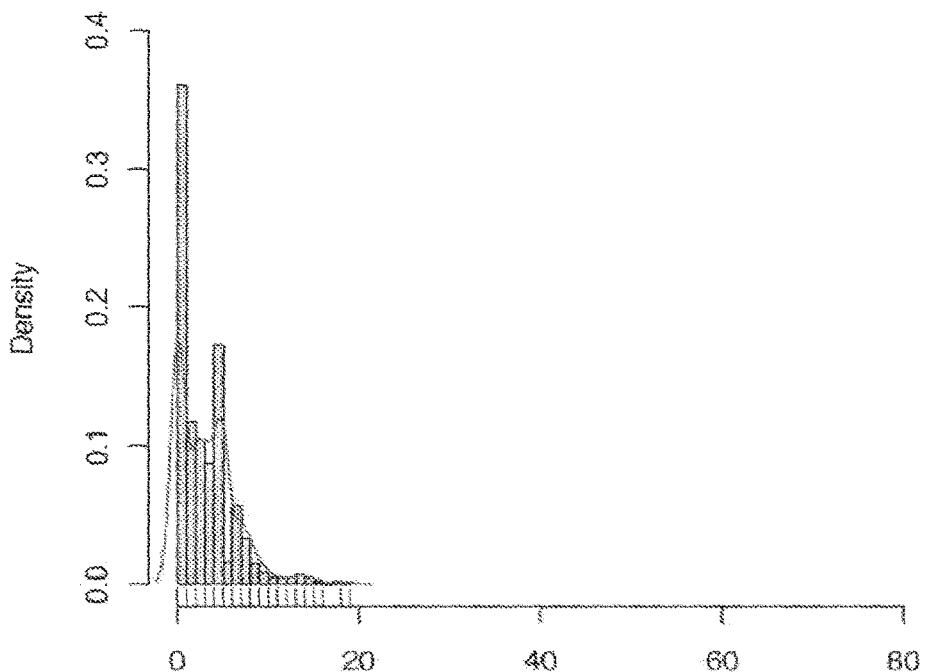

For confirmation of the repeat expansion and to estimate its size, fluorescence in situ hybridization (FISH) was performed in an affected member of the GWENT#1 kindred (III-1, FIG. 1A, ND06769), in a case from the NINDS0760 pedigree (III-1, FIG. 1E), and in neurologically normal controls (ND11463, ND08559, ND03052, and ND03053). These experiments used a fluorescently-labeled oligonucleotide probe consisting of three GGGGCC repeats (Haaf et al., 1996). All metaphases of the cases showed a strong hybridization signal to a single chromosome—9p21—consisting of a discrete dot on each sister chromatid (FIG. 2C). Fluorescence was not detected in any metaphases of the control samples. These experiments indicated that the expansion was at least 1.5 kilobase (kb) in size, which is the minimum detectable size of a repeat using this technique (Liehr, (2009 FISH Application Guide (Berlin: Springer-Verlag).

Figure 1C:
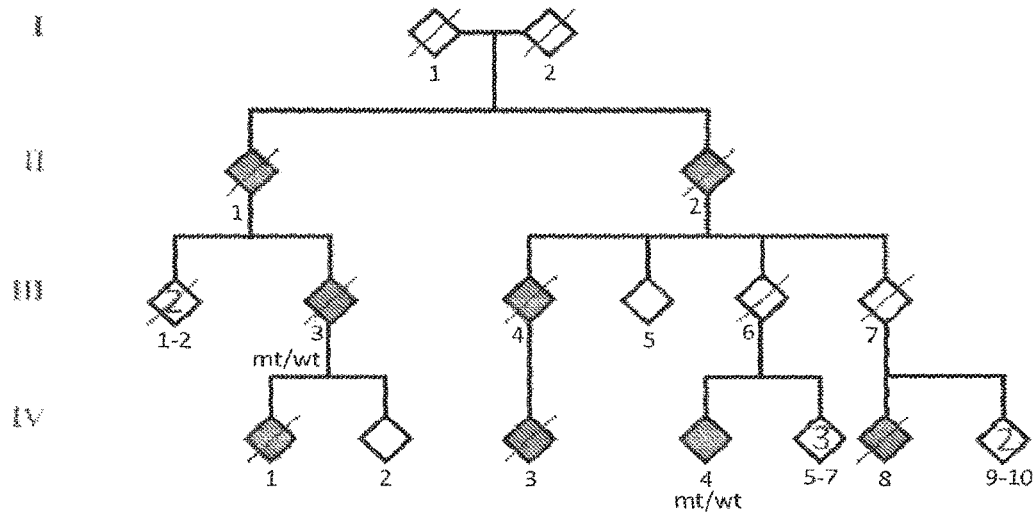
Figure 1D:
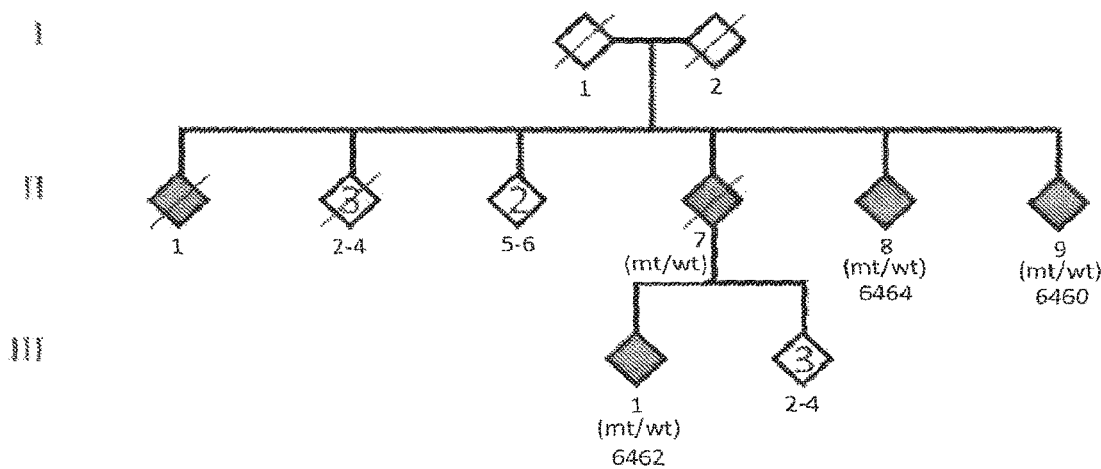
Figure 3C:
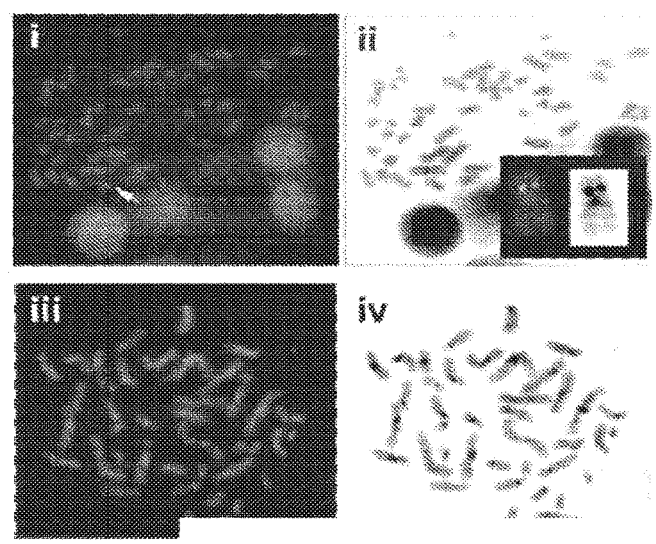

The data clearly showed the importance of the hexanucleotide repeat expansion within the Finnish ALS population and in families linked to the chromosome 9p21 region. To further determine the frequency of the hexanucleotide expansion in outbred European populations, we screened a cohort of 260 familial ALS probands from North America (n=198), Germany (n=36) and Italy (n=26) using repeat-primed PCR. 98 (37.7%) of these cases carried the same hexanucleotide GGGGCC repeat expansion within C9ORF72 (FIG. 3C). Within this dataset, we identified three additional multi-generational families where the presence of the repeat expansion segregated perfectly with disease within the kindred (FIGS. 1C, 1D and 1E). In contrast, the repeat expansion was not detected in 242 US controls, 83 Italian controls and 64 German controls (total number of control chromosomes=778, average number of repeats=3, range 0 to 19, FIG. 3D). An additional series of 300 anonymous African and Asian samples that are part of the Human Gene Diversity Panel (Cann et al., 2002) were included in the mutational analysis as controls to evaluate the genetic variability of the C9ORF72 hexanucleotide repeat expansion in non-Caucasian populations. None of these samples carried more than 15 GGGGCC repeats (average number of repeats=3, range=0-15).

Given the genetic and clinical overlap between ALS and FTD, as well as the co-occurrence of ALS and FTD within families linked to the chromosome 9p21 locus, we tested the hypothesis that the hexanucleotide repeat expansion may underlie a proportion of FTD cases by measuring its occurrence in a cohort of 75 Finnish FTD cases using the same repeat primer PCR method. The percentage of these FTD cases carrying the repeat expansion was comparable to that of the Finnish ALS cohort (n=22, representing 29.3% of the cohort), and the GGGGCC repeat expansion was highly associated with FTD in the Finnish population (fisher p-value based on 75 Finnish FTD cases and 478 Finnish controls=4.327×10$^{-18}$; OR=82.0, 95% CI 19.1-352.8). Six of the Finnish FTD cases carrying the repeat expansion presented with progressive non-fluent aphasia, and the remaining 16 patients had clinical features consistent with behavioral-variant FTD. In addition, 8 (36.4%) of these Finnish FTD patients had a personal or family history of ALS.

Using expression arrays, C9ORF72 RNA was detected across multiple CNS tissues obtained from neuropathologically normal individuals including spinal cord, with the highest expression level observed within the cerebellum (FIG. 5A). Immunohistochemistry using an antibody that recognizes both human and mouse C9ORF72 (Santa Cruz Biotechnology, Inc.) found the protein to be predominantly localized within the nucleus in both human fibroblast cell lines and in the mouse motor neuron NSC-34 cell line (FIGS. 5A & B). Immunoblotting confirmed that C9ORF72 is mainly situated within the nucleus with only modest cytosolic staining observed in fibroblasts derived from neurologically normal individuals (FIG. 5C).

Alterations of C9ORF72 RNA expression and protein levels in fibroblast and lymphoblastoid cell lines from patients were examined by real-time RT-PCR and immunoblotting. We found a ~50% decrease in C9ORF72 RNA expression in frontal cortex of an affected case from the GWENT kindred compared to neurologically normal controls (FIG. 4B). In contrast, expression of nearby LINGO2 gene was not altered in the same case (data not shown). Additional analysis in lymphoblastoid cell lines revealed that this decrease was entirely due to a reduced level of the short transcript of C9ORF72 (NM_145005.4) suggesting that the position of the GGGGCC repeat expansion within the intron of this gene disrupts transcription (FIG. 4C). Immunocytochemistry and immunoblotting confirmed that overall C9ORF72 protein levels were reduced in fibroblast cell lines derived from ALS patients relative to controls, and that there was less nuclear and relatively more cytoplasmic staining in cases compared to controls (FIGS. 5B and C).

1.4 Discussion

The inventors used used next-generation sequencing technology to identify a hexanucleotide repeat expansion within the C9ORF72 gene as the cause of chromosome 9p21-linked ALS-FTD, and subsequently confirmed the presence of this large expansion in a substantial proportion of familial ALS and FTD cases. Overall, the hexanucleotide repeat expansion was found in nearly one half of Finnish familial ALS cases and in more than one third of familial ALS cases of wider European ancestry. Our data indicate that the repeat expansion is more than twice as common as mutations in the SOD) gene as a cause of familial ALS (Chiö et al., (2008) Neurology 70 p533-537, and more than three times as common as TARDBP, FUS, OPTN and VCP mutations combined. Taken together with the D90A SOD1 mutation, our data show that nearly 90% of familial ALS in Finland is now explained by a simple monogenic cause.

We present five pieces of genetic data demonstrating that the hexanucleotide repeat expansion is pathogenic for neurodegeneration. First, the hexanucleotide expansion segregated with disease within two multi-generational kindreds that have been convincingly linked to the region (Pearson et al., 2011 supra). Second, the hexanucleotide expansion was highly associated with disease in the same cohort of ALS cases and controls that was used to identify the chromosome 9p21 region within the Finnish population. Furthermore, the association signal based on the presence or absence of the expansion was many times greater than that indicated by the surrounding SNPs (trend test p-value based on expansion=8.1×10$^{-38}$ versus 9.11×10$^{-11}$ based on the most associated SNP rs3849942 in the initial Finnish ALS GWAs) (Laaksovirta et al., 2010 supra). Third, the hexanucleotide repeat expansion was not found in 389 population-matched control subjects or in 300 diverse population samples screened in our laboratory. Fourth, we found that a large proportion of apparently unrelated familial ALS and FTD cases carried the same hexanucleotide repeat expansion within C9ORF72. Within this cohort of European-ancestry familial samples, we identified three additional multi-generational families within which the repeat expansion segregated perfectly with disease. Fifth, FISH analysis demonstrated that the repeat expansion is large in size (at least 1.5 kb to be visualized by this technique, FIG. 2C), and such long expansions are typically pathogenic (Kobayashi et al., 2011 supra).

Our data indicate that both ALS and FTD phenotypes are associated with the C9ORF72 GGGGCC hexanucleotide repeat expansion. Several members of the GWENT#1 and DUTCH#1 pedigrees manifested clinical signs of isolated motor neuron dysfunction or isolated cognitive decline, whereas other affected members developed mixed ALS-FTD symptomotology over the course of their illness (Pearson et al., 2011 supra). It is interesting to note that the frequency of the repeat expansion was almost identical in our ALS and FTD case cohorts, suggesting that carriers of the mutant allele are equally at risk for both forms of neurodegeneration. Our data supports the notion that the observed clinical and pathological overlap between ALS and FTD forms of neurodegeneration may be driven in large part by the C9ORF72 hexanucleotide repeat expansion.

The identification of the cause of chromosome 9p21-linked neurodegeneration allows for future screening of population-based cohorts to further unravel the overlap between ALS and FTD, and to identify additional genetic and environmental factors that push an individual's symptoms towards one end of the ALS/FTD clinical spectrum. Some early observations may already be made: among our Finnish FTD cohort, we identified several patients carrying the pathogenic repeat expansion who presented with non-fluent progressive aphasia. This suggests that the difficulties with speech production that are commonly observed in ALS patients may in some cases be partially attributable to cortical degeneration in addition to tongue and bulbar musculature weakness secondary to hypoglossal motor neuron degeneration.

Our development of a rapid, reliable method of screening individuals for the repeat expansion will have immediate clinical utility by allowing early identification of ALS patients at increased risk of cognitive impairment, and of FTD cases at increased risk of progressive paralysis. In the longer term, the identification of the genetic lesion underlying chromosome 9p21-linked ALS and FTD, together with the observed high frequency in these patient populations, makes it an ideal target for drug development aimed at amelioration of the disease process.

Broadly speaking, pathogenic repeat expansions are thought to cause disease through haploinsufficiency, in which expression or splicing of the target gene is perturbed, or through the generation of abnormal amounts of toxic RNA that disrupt normal cellular pathways. We favor the second as a mechanism in chromosome 9 FTD/ALS, given the large size of the expansion visualized by FISH and its non-coding localization within the C9ORF72 gene. RNA generated from such pathogenic repeat expansions are thought to disrupt transcription by sequestering normal RNA and proteins involved in transcription regulation and disruption of RNA metabolism has already been implicated in the pathogenesis of ALS associated with mutations in TDP-43 and FUS (Lagier-Tourenne et al., (2010) Human Molecular Genetics 19 R46-64). However, knowing the pattern of distribution of C9ORF72 expression is likely to be key in understanding cell vulnerability and local expression of the hexanucleotide repeat expansion, which is likely influenced by the promoter of the C9ORF72 gene. Additional molecular biology investigation is required to understand the precise mechanism by which the hexanucleotide repeat may disrupt RNA metabolism, and to determine the relevance of altered C9ORF72 expression in neuronal death.

An important aspect of understanding a pathogenic repeat expansion focuses on its stability. Preliminary evidence suggests that the C9ORF72 hexanucleotide repeat expansion may be unstable. First, minor anticipation has been noted in pedigrees that originally identified the locus with earlier generations being relatively unaffected by disease, perhaps reflecting expanding repeat number over successive generations (Vance et al., 2006). Second, although there was strong concordance between the presence of the chromosome 9p21 founder risk haplotype and the presence of the hexanucleotide expansion in an individual, the expansion was also present in ALS cases that did not carry this haplotype. These data are consistent with the expansion occurring on multiple occasions on multiple haplotype backgrounds. Taken together, these observations suggest that the C9ORF72 repeat region has some degree of instability. This instability may be particularly relevant for sporadic ALS, where the apparent random nature of the disease in the community could be a consequence of stochastic expansion in the number of repeats. It is noteworthy that a sizeable proportion of the Finnish ALS cases that carried the repeat expansion was clinically classified as sporadic.

In summary, our data demonstrate that a massive hexanucleotide repeat expansion within C9ORF72 is the cause of chromosome 9p21-linked ALS, FTD and ALS-FTD. Furthermore, this expansion accounts for an unprecedented proportion of ALS cases in Finland and in familial ALS cases of European ancestry, and provides additional evidence supporting the role of disrupted RNA metabolism as a cause of neurodegeneration.

EXAMPLE 2: SOUTHERN BLOTT ANALYSIS OF C9ORF72 GENE MUTATIONS

The inventors developed a Southern Blott procedure for identifying expansions of hexanucelotide repeats as a preferred method of conducting prognostic and diagnostic test according to the invention.

2.2 Methods.
2.2.1 Non-Radioactive Labelling of DNA Products with Digoxigenin
2.2.1 (a) Reagents:
  0.2M EDTA (ph 8.0).
  Maleic Acid Buffer (0.1M Maleic acid, 0.15M NaCl, adjusted with NaOH to ph 7.5)
  Blocking solution (Maleic Acid Buffer plus 1% blocking powder (roche), dissolve block at 65° C. with stirring and cool to room temperature before use, the solution will keep in frozen aliqots.
  Antibody solution (Blocking solution plus antibody at 1:10,000 dilution)
  Detection buffer (0.1M Tris HCl, 0.1M NaCl, pH 9.5).
  CSPD detection solution (Dilute CSPD 1:100 in detection buffer, this will keep for up to a month at 4° C., wrap in foil to protect from light).
2.2.1 (b) Protocol:
  1. Add 10 ng to 3 µg of template DNA to a 1.5 ml eppendorf. (At least 300 ng is required for a southern blot, for single copy genes). Make the volume up to 15 µl with molecular grade water.
  2. Denature the sample using wet heat for 10 minutes, and chill the sample on an ice/water bath to prevent re-annealing of the DNA.

3. Add the following to the freshly denatured DNA.
   2 µl hexanucleotide mix (10×)
   2 µl dNTP labelling mix
   1 µl klenow enzyme
4. Mix the contents briefly, and settle by centrifugation, and incubate for 1 hr to 20 hr at 37° C.
5. Stop the reaction by adding 2 µl of 0.2M EDTA (ph 8.0), or by heating the reaction to 65° C. for 10 minutes.

The amount of labelled product that is required will depend on the amount of starting material as shown in Table 2.

TABLE 2

| Template DNA | Labelling time | |
|---|---|---|
| | 1 hr | 20 hr |
| 10 ng | 15 ng | 50 ng |
| 30 ng | 30 ng | 120 ng |
| 100 ng | 60 ng | 260 ng |
| 300 ng | 120 ng | 450 ng |
| 1000 ng | 260 ng | 780 ng |
| 3000 ng | 530 ng | 890 ng |

2.2.1 (c) Quantifying the Amount of Labelled DNA:

To determine the amount of labelled probe the dilutions of the control labelled DNA and labelling reactions were made up as illustrated in Table 3.

TABLE 3

| Tube | DNA | DNA dilution buffer | Dilution of control | Final concentration |
|---|---|---|---|---|
| Reaction or control (1) | 1 µl | — | neat | 1 ng/µl |
| 2 | 1 µl of tube 1 | 9 ul | 1:10 | 0.1 ng/µl (100 pg/µl) |
| 3 | 1 µl of tube 2 | 9 ul | 1:100 | 10 pg/µl |
| 4 | 1 µl of tube 3 | 9 ul | 1:1000 | 1 pg/µl |
| 5 | 1 µl of tube 4 | 9 ul | 1:10000 | 0.1 pg/µl |
| 6 | 1 µl of tube 5 | 9 ul | 1:100000 | 0.01 pg/µl |

Procedure:
1. Spot 1 µl of each dilution onto a small piece of nylon membrane for both your labelling reaction and control DNA and allow to air dry.
2. Cross link the DNA to the membrane by placing the membrane face down on the UV transilluminator for 90 seconds. (Note the illuminator was calibrated in 2009, the cross linking efficiency should be checked at least once a year).
3. Place the membrane in a petri dish and incubate the membrane with shaking in Washing buffer for 1 minutes.
4. Incubate the membrane for 10 minutes in blocking solution
5. Incubate the membrane for 10 minutes in antibody solution.
6. Wash the membrane twice (2×5 minutes) in washing buffer
7. Equilibrate the membrane for 2 minutes in detection buffer
8. Place the membrane DNA side up on a sheet of acetate and add 100 µl of CSPD solution, and cover the membrane with a second sheet of acetate, being careful to eliminate bubbles. (note: CSPD is used at 1 ml per 100 cm² so if you have a large dot blot you may need more CSPD solution).
9. Incubate the membrane at 37° C. for 10 minutes, then image the membrane for 15-25 minutes.
10. By comparing the intensity of the control labelled DNA and your labelling reactions you can estimate the concentration of your labelled DNA.

2.2.2 Southern Blotting/Hybridization and Detection of Nylon Membranes 2.2.2 (a) Reagents:

Depruination solution (0.25M HCl) (10 mls of conc HCl in 500 ml of water)

Gel Denaturing solution (0.6M NaCl, 0.2N NaOH) (17.53 g of NaCl, 4 g NaOH in 500 ml)

Gel neutralizing solution (1.5M NaCl, 0.5M Tris-HCl pH8.0) (43.8 g NaCl, 30.30 g Tris, ph to 8.0 with HCl).

20×SSC stock (3M NaCl, 300 mM Sodium citrate pH 7.4 (175.3 g of NaCl, 88.2 g of sodium citrate per liter of water).

Dig easy Hybridization buffer (Roche)

Maleic Acid Buffer (0.1M Maleic acid, 0.15M NaCl), (23.22 g Maleic acid, 17.53 g NaCl, adjusted with NaOH to ph 7.5)

Blocking solution (Maleic Acid Buffer plus 1% blocking powder (roche), dissolve block at 65° C. with stirring and cool to room temperature before use, the solution will keep in frozen aliquots.

Antibody solution (Blocking solution plus antibody at 1:10,000 dilution) using antibody: sc-138763 from Santa Cruz Biotechnology Inc.; HPA023873 from Sigma-Aldrich; or GTX119776 from GeneTex Detection buffer (0.1M Tris HCl, 0.1M NaCl, pH 9.5) (make up from 1M Tris Ph9.5 stock, and 5M NaCl stock)

CSPD detection solution (Dilute CSPD 1:100 in detection buffer).

Blot stripping solution (0.2M NaOH; 0.1% SDS) (4 g NaOH, 5 mls 10% SDS solution in 500 ml)

2.2.2(b) Blotting DNA Samples
1. Samples should be electrophoresed on an appropriate percentage agarose gel for resolution, generally southern blotting is carried out for genomic DNA digests that should be run on 0.8% gels.
2. Photograph the gel with a ruler next to the marker to allow for band size determination at a later date if required. Cut a corner off your gel before photography to allow the blot to be orientated after hybridization. The gel can also be trimmed at this stage to optimize the use of membrane which is expensive.
3. To blot fragments larger than 10 Kb depurinate the gel by Inverting the gel into a solution of 0.25M HCl for 10 min or until the bromophenol blue turns yellow, briefly rinse the gel before the next step in water.
4. Denature the DNA in the gels by shaking the gel slowly for 30 minutes in gel denaturing solution.
5. Neutralize the gel by shaking slowly for 30 minutes in gel neutralizing solution.
6. While the gel is shaking prepare 3 sheets of whatman 3 MM paper and a sheet of nylon membrane the same size as your gel, plus another strip the same width but approximately 1.5× the length, and 15 sheets of extra thick blotting paper of the same size.
7. At this point you can cut a corner off your membrane to allow the blot to be orientated after hybridization.
8. Using 10×SSC assemble the southern blot.
   Place the longer strip of filter paper as a bridge to allow the 10×SSC in the buffer reservoir to wick up into the gel. Place your gel on the bridge, followed by your nylon membrane—being careful to remove all bubbles between the gel and membrane. Follow by the sheets of 3 MM paper and your extra thick blotting paper. Place a weight on top of the paper and leave the gel overnight to transfer.
9. After blotting disassemble the blot (the 10×SSC can be kept for re-use), and gently wash the blot in 2×SSC. Using gloves any agarose can be gently removed.
10. Wash the blot in 2×SSC twice for 15 minutes each wash. Gently air dry the membrane and UV fix, DNA side down on the transilluminator for 90 seconds.
11. Membranes can be stored between sheets of 3 MM paper for later hybridization.

2.2.2 (c) Hybridization
1. Before commencing measure your membrane, for each 100 cm$^2$ you will need 10 ml of DIG easy hyb for pre-hybridization, and 3.5 ml for hybridization (roller bottles require a minimum of 6 ml in the bottle). Pre-warm the solution to 42° C. before use.
2. Using the roller bottles, place your membrane DNA side facing inwards, add the appropriate volume of pre-warmed hyb solution and incubate the blot for a minimum of 30 minutes. (Note this can be left a few hours if required, prehybridization blocks the non-specific sites on the membrane and reduces the background.)
3. Using 25 ng of labelled probe per ml of required hybridization solution (150 ng for 6 ml), add 50 ul of molecular biology grade water. Denature the probe in a boiling water bath for 5 minutes, and chill on an ice/water bath immediately. Immediately add the probe to your pre-warmed hybridization solution and replace the pre-hyb solution with this. Hybridize the blot overnight for genomic DNA, 3 hours will be sufficient for plasmid targets. Make up your post hybridization solutions and leave in the hybridization oven to use the next day ready warmed.
4. After hybridization pour off the probe (this can be saved for re-use up to 5 times), and wash your blots to remove non-specific probe binding. (Rinsing the membrane in the bottle with 2×SSC; 0.1% SDS can reduce background).
5. Low stringency wash.
Remove the blot to a clean plastic tray and add sufficient low stringency wash buffer (2×SSC, 0.1% SDS) to cover the blot and incubate with shaking for 10 minutes. Replace the buffer with fresh and incubate with shaking for an additional 5 minutes.
6. High stringency washes
As a starting point two 15 minute washes using a 0.5×SSC 0.1% SDS wash solution pre-warmed to 65° C. is a good place to start. If background after detection is high a more stringent wash can be used. Stringency is increased by decreasing the salt concentration and increasing the temperature, thus a 0.1×SSC, 0.1% SDS wash is more stringent than a 0.5×SSC, 0.1% SDS wash.

2.2.2(d) Chemiluminescent Detection
11. Place the membrane in a clean container dish and incubate the membrane with shaking in washing buffer for 2 minutes. (To reduce background you can quickly rinse off the stringency wash buffer with wash buffer before this step).
12. Incubate the membrane for 30 minutes in 100 ml of blocking solution
13. Incubate the membrane for 30 minutes in 20 ml of antibody solution. (Before use of antibody aliquot spin the tube at high speed for 5 minutes to remove any complexed antibody.)
14. Wash the membrane twice (2×15 minutes) in washing buffer. (To reduce background you can quickly rinse off the stringency wash buffer with wash buffer before this step).
15. Equilibrate the membrane for 5 minutes in detection buffer
16. Place the membrane DNA side up on a sheet of acetate and add 1 ml of CSPD solution per 100 cm$^2$ of membrane, and cover the membrane with a second sheet of acetate, being careful to eliminate bubbles.
17. Incubate the membrane at 37° C. for 10 minutes, then image the membrane initially for 15-25 minutes.

2.3 Results
The inventors analysed samples from subjects suffering from the two main subgroups of FTLD (i.e. subjects with MND/ALS and/or FTD) and were able to observe, and quantify, the number of GGGGCC repeat in diseased subjects. The hexanucleotide was significantly expanded over control samples (from subjects without FTLD). Some affected individuals had several hundred repeats and some had more than 1,000 repeats (e.g. about 4,000 repeats) when compared to control samples which typically had 1-25 GGGGCC repeat.

FIG. 6 is an illustrative example of a Southern Blot analysis of samples from a subject with MND/ALS. The figure shows an expansion of approximately 1100 repeats (approximately 9 kb) in tissue from different brain regions of an ALS subject (F=frontal; T=temporal; and O=Occipital) and cell line controls (+ and −ve for the repeat).

FIG. 7 is a further illustrative example of Southern Blot analysis of samples from subjects with ALS/MND and/or FTD. The data from the figure was quantified and is summaried further in Table 4.

TABLE 4

| Lane | Source of Sample | Size of nucleic acid (bp) | Approximate No of repeats |
|---|---|---|---|
| 1 | Subject with MND/ALS | 14434 | — |
| 2 | Digestion failure | 397 | — |
| 3 | Subject with MND/ALS and FTD | 5234 and 3553 | 2005-485 |
| 4 | Positive Control | — | 2190 |
| 5 | Negative Control | 0 | 0 |
| 6 | Subject with FTD (age of onset 52) | 6572-25000 | 700-+3800 |
| 7 | Subject with FTD (age of onset 56) | 6644-18490 | 720-2700 |

The data from lanes 6 and 7 support the inventors view that the age of onset of disease may be earlier in subject with the greatest number of GGGGCC repeats.

The invention claimed is:

1. A method of detecting a hexanucleotide repeat GGCCCC or GGGGCC in the C9orf72 gene or mRNA, the method comprising:
   obtaining a sample from a subject;
   mixing the sample with a labeled nucleic acid oligonucleotide having a nucleic acid sequence comprising GGCCCCGGCCCC (SEQ ID NO: 13) or GGGGCCGGGGCC (SEQ ID NO: 14); and
   detecting in the C9orf72 gene the hybridization of the labeled nucleic acid oligonucleotide to the hexanucleotide repeat starting at position 27,573,527 (coordinate taken from GRCh37/Hg19, forward strand).

2. The method of claim 1, wherein the hybridization of the labeled nucleic acid oligonucleotide is detected by polymerase chain reaction, quantitative polymerase chain reaction, sequence specific oligonucleotide hybridization, reference strand mediated conformational analysis, Southern blotting, or a combination thereof.

3. The method of claim 1, wherein the nucleic acid sequence comprises GGCCCCGGCCCCGGCCCC (SEQ ID NO: 15) or GGGGCCGGGGCCGGGGCC (SEQ ID NO: 16).

4. The method of claim 1, wherein the nucleic acid sequence of the labeled nucleic acid oligonucleotide comprises SEQ ID NO: 7.

5. A method of diagnosing a subject as having or at increased risk of developing Frontotemporal Lobar Degeneration (FTLD) or Motor Neuron Disease (MND)/Amyotrophic Lateral Sclerosis (ALS), the method comprising:
   obtaining a sample from a subject;
   mixing the sample with a labeled nucleic acid oligonucleotide having a nucleic acid sequence comprising GGCCCCGGCCCC (SEQ ID NO: 13) or GGGGCCGGGGCC (SEQ ID NO: 14);
   detecting in the C9orf72 gene the hybridization of the labeled nucleic acid oligonucleotide to the hexanucleotide repeat starting at position 27,573,527 (coordinate taken from GRCh37/Hg19, forward strand), wherein increased binding of the nucleic acid oligonucleotide is indicative of a subject having the hexanucleotide repeat; and
   diagnosing a subject as having or at increased risk for developing at least one of FTLD, MND/ALS, or a combination thereof, when at least 30 hexanucleotide repeats are detected in a sample obtained from the subject.

6. The method of claim 5, wherein the nucleic acid sequence comprises GGCCCCGGCCCCGGCCCC (SEQ ID NO: 15) or GGGGCCGGGGCCGGGGCC (SEQ ID NO: 16).

7. The method of claim 5, wherein the subject that has or is at increased risk of developing FTLD, MND/ALS or a combination thereof has at least 100 repeat copies of the hexanucleotide.

8. The method of claim 5, wherein the subject that has or is at increased risk of developing FTLD, MND/ALS or a combination thereof has at least 500 repeat copies of the hexanucleotide.

9. The method of claim 5, wherein the subject that has or is at increased risk of developing FTLD, MND/ALS or a combination thereof has at least 600 repeat copies of the hexanucleotide.

10. The method of claim 5, wherein the subject that has or is at increased risk of developing FTLD, MND/ALS or a combination thereof has at least 700 repeat copies of the hexanucleotide.

11. The method of claim 5, wherein the subject that has or is at increased risk of developing FTLD, MND/ALS or a combination thereof has at least 1,000 repeat copies of the hexanucleotide.

12. The method of claim 5, wherein the FTLD is frontotemporal dementia (FTD) or FTLD with motor neuron disease/amyotrophic lateral sclerosis (MND/ALS).

13. The method of claim 5, wherein the hybridization of the labeled nucleic acid oligonucleotide was detected by polymerase chain reaction, quantitative polymerase chain reaction, sequence specific oligonucleotide hybridization, reference strand mediated conformational analysis, southern blotting, or a combination thereof.

14. A method of diagnosing a subject as having or at increased risk of developing Frontotemporal Lobar Degeneration (FTLD) or Motor Neuron Disease (MND)/Amyotrophic Lateral Sclerosis (ALS), the method comprising:
   obtaining a sample from a subject;
   mixing the sample with a labeled nucleic acid oligonucleotide having a nucleic acid sequence comprising SEQ ID NO: 7;
   detecting in the C9orf72 gene the hybridization of the labeled nucleic acid oligonucleotide to the hexanucleotide repeat starting at position 27,573,527 (coordinate taken from GRCh37/Hg19, forward strand), wherein increased binding of the nucleic acid oligonucleotide is indicative of a subject having the hexanucleotide repeat and
   diagnosing a subject as having or at increased risk for developing at least one of FTLD, MND/ALS, or a combination thereof, when at least 30 hexanucleotide repeats are detected in a sample obtained from the subject.

15. The method of claim 14, wherein the subject that has or is at increased risk of developing FTLD, MND/ALS or a combination thereof has at least 100 repeat copies of the hexanucleotide.

16. The method of claim 14, wherein the subject that has or is at increased risk of developing FTLD, MND/ALS or a combination thereof has at least 500 repeat copies of the hexanucleotide.

17. The method of claim 14, wherein the subject that has or is at increased risk of developing FTLD, MND/ALS or a combination thereof has at least 600 repeat copies of the hexanucleotide.

18. The method of claim 14, wherein the subject that has or is at increased risk of developing FTLD, MND/ALS or a combination thereof has at least 700 repeat copies of the hexanucleotide.

19. The method of claim 14, wherein the subject that has or is at increased risk of developing FTLD, MND/ALS or a combination thereof has at least 1,000 repeat copies of the hexanucleotide.

20. The method of claim 14, wherein the FTLD is frontotemporal dementia (FTD) or FTLD with motor neuron disease/amyotrophic lateral sclerosis (MND/ALS).

* * * * *